US012734465B2

(12) United States Patent
Katz et al.

(10) Patent No.: US 12,734,465 B2
(45) Date of Patent: Sep. 15, 2026

(54) BIOPROCESS WITH REDUCED FOULING ON SURFACES

(71) Applicant: NUTRITION & BIOSCIENCES USA 1, LLC, Rochester, NY (US)

(72) Inventors: Joshua S. Katz, Merion Station, PA (US); Susan L. Jordan, Doylestown, PA (US); Hadi Fares, Philadelphia, PA (US); Benjamin Yezer, Conshohocken, PA (US)

(73) Assignee: Nutrition & Biosciences USA 1, LLC, Wilmington, DE (US)

( * ) Notice: Subject to any disclaimer, the term of this patent is extended or adjusted under 35 U.S.C. 154(b) by 606 days.

(21) Appl. No.: 18/005,243

(22) PCT Filed: Jul. 14, 2021

(86) PCT No.: PCT/US2021/041508
§ 371 (c)(1),
(2) Date: Jan. 12, 2023

(87) PCT Pub. No.: WO2022/015779
PCT Pub. Date: Jan. 20, 2022

(65) Prior Publication Data

US 2023/0242580 A1 Aug. 3, 2023

Related U.S. Application Data

(60) Provisional application No. 63/052,048, filed on Jul. 15, 2020.

(51) Int. Cl.

| | |
|---|---|
| ***C07K 1/34*** | (2006.01) |
| ***B01D 15/26*** | (2006.01) |
| ***B01D 15/38*** | (2006.01) |
| ***B01D 61/14*** | (2006.01) |
| ***B01D 71/34*** | (2006.01) |
| ***B01D 71/68*** | (2006.01) |
| ***C07K 1/18*** | (2006.01) |
| ***C07K 16/06*** | (2006.01) |

(52) U.S. Cl.
CPC .............. *C07K 1/34* (2013.01); *B01D 15/265* (2013.01); *B01D 15/3809* (2013.01); *B01D 61/14* (2013.01); *B01D 71/34* (2013.01); *B01D 71/68* (2013.01); *C07K 1/18* (2013.01); *C07K 16/065* (2013.01)

(58) Field of Classification Search
CPC ............. B01D 15/08; C07K 1/34; C07K 1/16
See application file for complete search history.

(56) References Cited

U.S. PATENT DOCUMENTS 6,383,380 B1 * 5/2002 Kopf .................... B01D 15/361
210/659
2018/0273683 A1 * 9/2018 Katz ................ C08G 65/33324
2020/0179246 A1 * 6/2020 Liang ..................... A61K 8/062

FOREIGN PATENT DOCUMENTS

WO 2012-134987 A1 10/2012
WO 2017-044366 A1 3/2017
WO 2017-044367 A1 3/2017
WO 2018-156467 A1 8/2018
WO 2020/055679 * 3/2020
WO 2020-055679 A2 3/2020
WO 2021-118963 A1 6/2021

OTHER PUBLICATIONS

Atkin, et al., Journal of Colloid and Interface Science, vol. 266, pp. 236-244 (2003).
Blas, et al., Biotechnology and Bioengineering, vol. 115, pp. 2760-2770 (2018).
Elwing, et al., Journal of Colloid and Interface Science, vol. 128, pp. 296-300 (1989).
Hanson, et al., Molecular Pharmaceutics, vol. 17, pp. 4302-4311 (2020).

(Continued)

*Primary Examiner* — Margaret G Moore
(74) *Attorney, Agent, or Firm* — Arnold & Porter Kaye Scholer LLP

(57) ABSTRACT

This disclosure relates to a process which involves: (a) providing an aqueous solution of a protein and a polyalkoxy fatty acyl surfactant of formula I (I)

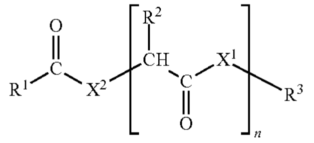

wherein $R^1$—C(═O) is a fatty acyl group, $R^2$ is H or a substituted or unsubstituted hydrocarbyl group, $X^1$ is O or NH, $X^2$ is O or NH, n is 0 or an integer of 1-5, $R^3$ is a polymeric group comprising polymerized units of formula II and III, (II)

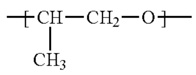

(III)

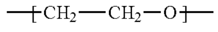

and (b) subjecting the aqueous solution to a bioprocess.

15 Claims, 14 Drawing Sheets

(56) References Cited

OTHER PUBLICATIONS

International Preliminary Report on Patentability for PCT/US2021/041508 (issued Jan. 17, 2023).
International Search Report for PCT/US2021/041508 (mailed Oct. 27, 2021).
Katz, AAPS PharmSci 360 presentation slides titled Surfactant Hydrophobe Variation Significantly Impacts Fundamental Performance and Biologic Stability (Oct. 27, 2020).
Katz, et al., AAPS PharmSci 360 poster titled Hydrophobe Variation in Surfactant Excipient Significantly Impacts Fundamental Performance and Biologic Stability in Liquid Formulation (2020).
Katz, Presentation slides for lecture at University of Pennsylvania titled Surfactant Innovation for Biologic Drug Products (2022).
Lei, et al., Biotechnology Progress, vol. 29(6), pp. 1503-1511 (2013).
Mahler, et al., Journal of Pharmaceutical Sciences, vol. 97(2), pp. 764-774 (2008).
Mahler, et al., Journal of Pharmaceutical Sciences, vol. 99(6), pp. 2620-2627 (2010).
Somasundaran, et al, The Journal of Physical Chemistry, vol. 68, pp. 3562-3566 (1964).
Tripathi, et al., Frontiers in Bioengineering and Biotechnology, vol. 7, Article 420, pp. 1-35 (2019).
Pall Laboratory, “Minimate™ Tangential Flow Filtration Capsule” (2020).
Wang, “Protein aggregation and its inhibition in biopharmaceutics,” *International Journal of Pharmaceutics*. 289(1-2), pp. 1-30 (Jan. 2005) (Amsterdam, Netherlands).
Zhou et al., “Non-specific binding and saturation of Polysorbate-20 with aseptic filter membranes for drug substance and drug product during mAb production,” *Journal of Membrane Science*. 325(2), pp. 735-741 (Dec. 2008) (Amsterdam, Netherlands).

* cited by examiner

Equilibrium Adsorption:

Reversible Adsorption:

BIOPROCESS WITH REDUCED FOULING ON SURFACES

BACKGROUND

Field of the Disclosure

The present disclosure relates to a method of using a polyalkoxy fatty acyl surfactant to reduce fouling of surfaces in a bioprocess.

Description of Related Art

Biologics, pharmaceuticals derived from proteins or other biologically-derived macromolecules, have rapidly emerged as an important class of pharmaceuticals as a result of their enhanced selectivity and diminished side effects compared to traditional small molecule drugs. Due to the relatively fragile nature of protein materials, development of biologic actives that are both therapeutically beneficial and sufficiently stable to withstand processing, distribution, and administration remains a significant challenge. Surfactants can be used to stabilize and protect proteins in solution by preventing protein adsorption onto interfaces or by forming protective structures in solution. However, surfactants are often incompatible with many steps of the process to produce the biologic, leading to them not being added until very late in the process (e.g., final formulation). For example, surfactants can interfere with bioprocesses by adsorbing irreversibly onto surfaces, leading to fouling of the surface, clogging of pores/membranes/filters, and reducing surfactant concentration in solution, limiting its ability to protect the protein in solution or further downstream. Fouling and clogging can additionally lead to longer down-times for cleaning, reducing throughput and productivity in the process. In some situations, biologics need to have access to and/or interact with a surface (e.g., a chromatography column or a filter) which is not blocked by the surfactants.

BRIEF SUMMARY OF THE DISCLOSURE

The present disclosure provides a process which comprises: (a) providing an aqueous solution comprising a protein and a polyalkoxy fatty acyl surfactant of formula I (I)

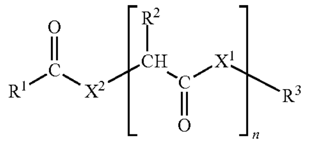

wherein $R^1$—C(=O) is a fatty acyl group, $R^2$ is H or a substituted or unsubstituted hydrocarbyl group, $X^1$ is O or NH, $X^2$ is O or NH, n is 0 or an integer of 1-5, $R^3$ is a polymeric group comprising polymerized units of formula II and III, (II)

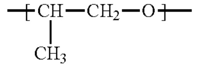

-continued (III)

$$-[CH_2-CH_2-O]-$$

and (b) subjecting the aqueous solution to a bioprocess.

BRIEF DESCRIPTION OF THE FIGURES

Embodiments are illustrated in the accompanying figures to improve understanding of concepts as presented herein.

FIG. 4 shows QCM-D data.

FIG. 5 depicts adsorption steps of IgG and surfactant as tail length increases. In each set of diagrams, the leftmost one depicts short tail length surfactant and IgG, the middle one depicts middle tail length surfactant and IgG, and the rightmost one depicts long tail length surfactant and IgG.

FIG. 6 shows the recovery of surfactants passing through a PVDF filter.

FIG. 7 shows the recovery of surfactants passing through a PES filter.

FIG. 8 shows the recovery of surfactants passing through a sulfopropyl-functionalized cross-linked agarose (SP HP) column.

FIG. 9 shows the recovery of surfactants passing through a Protein A column.

FIG. 10 shows the recovery of surfactants passing through a quaternary ammonium-functionalized cross-linked agarose (Q HP) column.

DETAILED DESCRIPTION

Figure 1:
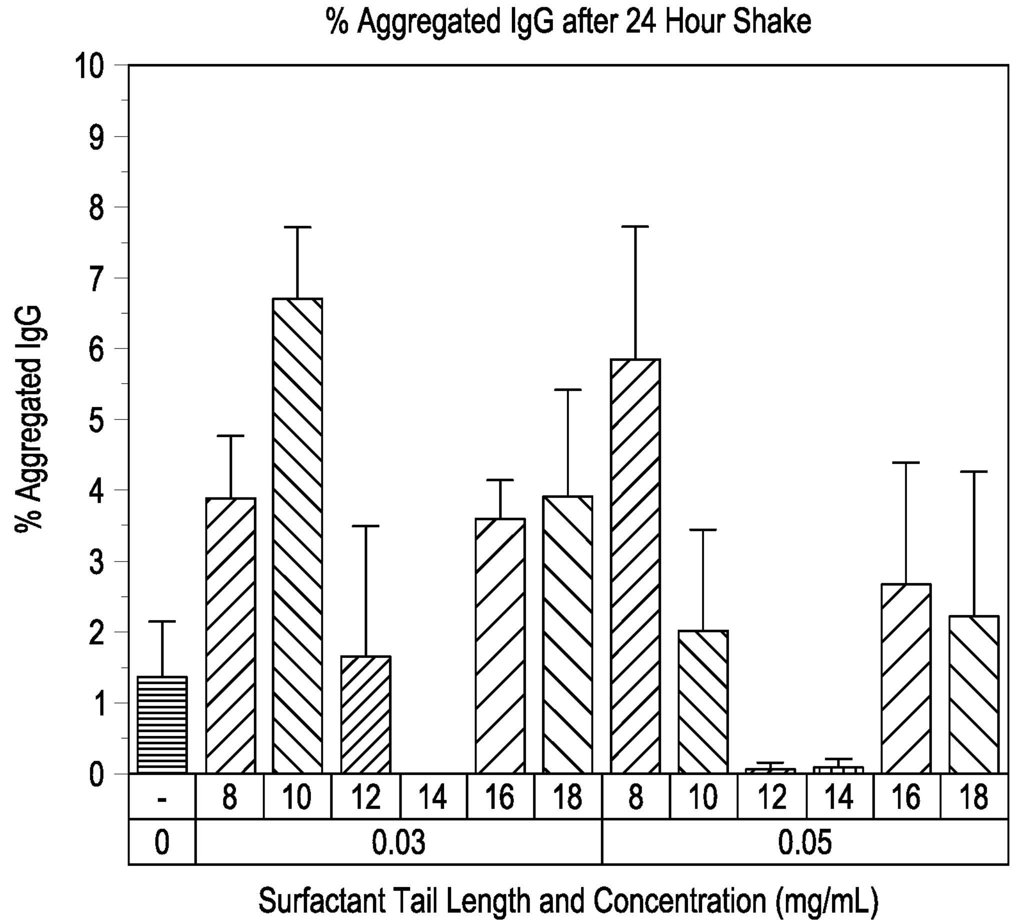
FIG. 1 shows percent aggregation of IgG (20 mg/mL) by different surfactant tail lengths at 0.03 mg/mL surfactant and 0.05 mg/mL surfactant in saline when shaken at room temperature for 24 hours as measured by DLS.

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. For example, when a range of "1 to 10" is recited, the recited range should be construed as including ranges "1 to 8", "3 to 10", "2 to 7", "1.5 to 6", "3.4 to 7.8", "1 to 2 and 7-10", "2 to 4 and 6 to 9", "1 to 3.6 and 7.2 to 8.9", "1-5 and 10", "2 and 8 to 10", "1.5-4 and 8", and the like.

The present disclosure illustratively described herein suitably may be practiced in the absence of any element or elements, limitation or limitations that are not specifically disclosed herein. While compositions and methods are described herein in terms of "comprising" various components or steps, the compositions and methods also can "consist essentially of" or "consist of" the various components or steps, unless stated otherwise.

Before addressing details of embodiments described below, some terms are defined or clarified.

The terms "surface" and "interface" are used interchangeably herein.

Number-average molecular weight is defined as the total weight of a sample divided by the number of molecules in the sample.

The term "surfactant/protein concentration ratio", as used herein, means the ratio of the concentration of polyalkoxy fatty acyl surfactant of formula I to the concentration of protein in an aqueous solution. The concentration of polyalkoxy fatty acyl surfactant of formula I and the concentration of protein are expressed as weight volume ratio (e.g., mg/ml) in the present disclosure.

A polyalkoxy compound is a compound that contains one or more group having the structure $-(\text{-A-O})_m—$, where m is three or more, and A is an unsubstituted alkyl group. The group A may be linear, branched, cyclic, or a combination thereof. The various A groups among the various -(-A-O)— groups may be the same as each other or different.

A fatty compound is a compound that contains one or more fatty group. A fatty group is a group that contains 8 or more carbon atoms, each of which is bonded to one or more of the other carbon atoms in the group. A polyalkoxy fatty compound is a compound that is both a polyalkoxy compound and a fatty compound.

A hydrocarbyl group is a group that contains hydrogen and carbon atoms. An unsubstituted hydrocarbyl group contains only hydrogen and carbon atoms. A substituted hydrocarbyl group contains one or more substituent group that contains one or more atom other than hydrogen and carbon.

A protein is a polymer in which the polymerized units are polymerized units of amino acids. The amino acids are bonded together by peptide bonds. A protein contains 20 or more polymerized units of one or more amino acid residues. The term protein includes linear polypeptide chains as well as more complex structures that contain polypeptide chains.

A protein is considered to be in solution in a liquid medium (or, synonymously, dissolved in the liquid medium) if the molecules of the protein are distributed throughout the continuous liquid medium in the form of dissolved individual molecules. The protein is considered to be dissolved in water if the continuous liquid medium contains water in the amount of 60% or more by weight based on the weight of the continuous liquid medium.

A chemical group is an ionic group if there is a pH value between 4.5 and 8.5 such that, when the chemical group is in contact with water at that pH value, 50 mole % or more of those chemical groups present are in ionic form.

A buffer is either (i) a compound that has the ability to accept a proton to form the conjugate acid of that compound, and the conjugate acid of that compound has pKa of less than 10, or (ii) a compound that has the ability to release a proton, and the compound has pKa of greater than 4.

The term “FM1000”, as used herein, means the polyalkoxy fatty acyl surfactant of formula I, wherein $R^1$ is $CH_3$—$(CH_2)_{11}$—$CH_2$—, n is 1, $X^1$ and $X^2$ are both NH, $R^2$ is —$CH_2(C_6H_5)$, and $R^3$ is a copolymer of PO and EO units capped with $CH_3$ with an approximate number-average molecular weight of 1000 and ratio of PO to EO of about 3:19. FM1000 has a 14-carbon length hydrophobic tail ($CH_3$—$(CH_2)_{11}$—$CH_2$—C(═O)).

The term “8FM1000”, as used herein, means the FM1000 derivative with 8 carbon hydrophobic tail, that is, 8FM1000 has the same chemical formula as FM1000 except $R^1$ is $CH_3$—$(CH_2)_5$—$CH_2$—. Similarly, the term “10FM1000”, as used herein, means the FM1000 derivative with 10 carbon hydrophobic tail, that is, 10FM1000 has the same chemical formula as FM1000 except $R^1$ is $CH_3$—$(CH_2)_7$—$CH_2$—; the term “12FM1000”, as used herein, means the FM1000 derivative with 12 carbon hydrophobic tail, that is, 12FM1000 has the same chemical formula as FM1000 except $R^1$ is $CH_3$—$(CH_2)_9$—$CH_2$—; the term “16FM1000”, as used herein, means the FM1000 derivative with 16 carbon hydrophobic tail, that is, 16FM1000 has the same chemical formula as FM1000 except $R^1$ is $CH_3$—$(CH_2)_{13}$—$CH_2$—; and the term “18FM1000”, as used herein, means the FM1000 derivative with 18 carbon hydrophobic tail, that is, 18FM1000 has the same chemical formula as FM1000 except $R^1$ is $CH_3$—$(CH_2)_{15}$—$CH_2$—.

The terms “FM1000” and “14FM1000” are used interchangeably herein.

The present disclosure provides a process which comprises: (a) providing an aqueous solution comprising a protein and a polyalkoxy fatty acyl surfactant of formula I (I)

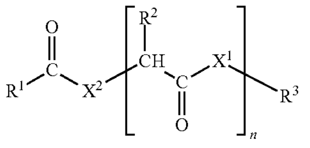

wherein $R^1$—C(═O) is a fatty acyl group, $R^2$ is H or a substituted or unsubstituted hydrocarbyl group, $X^1$ is O or NH, $X^2$ is O or NH, n is 0 or an integer of 1-5, $R^3$ is a polymeric group comprising polymerized units of formula II and III, (II)

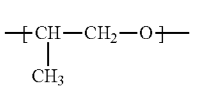

(III)

$$-\!\!\left[CH_2-CH_2-O\right]\!\!-$$

and (b) subjecting the aqueous solution to a bioprocess.

The term, “bioprocess”, as used herein, means the downstream part of a protein bioprocess where the protein from the upstream (e.g., biochemical production or synthesis) is processed to meet purity and quality requirements. The bioprocess includes storage, transportation and purification.

In some embodiments, the bioprocess is selected from the group consisting of transportation, filtration, chromatography, and combinations thereof.

The aqueous solution provided in step (a) comprises a protein and a polyalkoxy fatty acyl surfactant of formula I dissolved therein (e.g., dissolved in water). In some embodiments, the concentration of the polyalkoxy fatty acyl surfactant of formula I in the aqueous solution of step (a) is from 0.001 mg/ml to 1 mg/ml, or from 0.01 mg/ml to 0.1 mg/ml, or from 0.01 mg/ml to 0.05 mg/ml, based on the total volume of the aqueous solution. In some embodiments, the concentration of the polyalkoxy fatty acyl surfactant of formula I in the aqueous solution of step (a) is no more than 1 mg/ml, or no more than 0.5 mg/ml, or no more than 0.2 mg/ml, or no more than 0.1 mg/ml, or no more than 0.08 mg/ml, or no more than 0.06 mg/ml, or no more than 0.05 mg/ml, based on the total volume of the aqueous solution. In some embodiments, the concentration of the polyalkoxy fatty acyl surfactant of formula I in the aqueous solution of step (a) is at least 0.001 mg/ml, or at least 0.002 mg/ml, or at least 0.005 mg/ml, or at least 0.01 mg/ml, or at least 0.02 mg/ml, or at least 0.03 mg/ml, based on the total volume of the aqueous solution.

In some embodiments, the concentration of the protein in the aqueous solution of step (a) is from 0.0001 mg/ml to 300 mg/ml, or from 0.0001 mg/ml to 200 mg/ml, or from 0.0001 mg/ml to 150 mg/ml, or from 0.001 mg/ml to 100 mg/ml, or from 0.01 mg/ml to 100 mg/ml, or from 0.1 mg/ml to 50 mg/ml, or from 0.1 mg/ml to 30 mg/ml, or from 0.1 mg/ml to 10 mg/ml, or from 10 mg/ml to 30 mg/ml, based on the total volume of the aqueous solution. In some embodiments, the concentration of the protein in the aqueous solution of step (a) is no more than 300 mg/ml, or no more than 250 mg/ml, or no more than 200 mg/ml, or no more than 150 mg/ml, or no more than 100 mg/ml, or no more than 80 mg/ml, or no more than 50 mg/ml, or no more than 40 mg/ml, or no more than 30 mg/ml, or no more than 20 mg/ml, or no more than 10 mg/ml, based on the total volume of the aqueous solution. In some embodiments, the concentration of the protein in the aqueous solution of step (a) is at least 0.0001 mg/ml, or at least 0.001 mg/ml, or at least 0.002 mg/ml, or at least 0.005 mg/ml, or at least 0.01 mg/ml, or at least 0.02 mg/ml, or at least 0.05 mg/ml, or at least 0.1 mg/ml, or at least 0.2 mg/ml, or at least 0.5 mg/ml, or at least 1 mg/ml, or at least 2 mg/ml, or at least 5 mg/ml, or at least 10 mg/ml, based on the total volume of the aqueous solution. The concentration of polyalkoxy fatty acyl surfactant of formula I and the concentration of protein are expressed as weight volume ratio (e.g., mg/ml) in the present disclosure.

In the polyalkoxy fatty acyl surfactant of formula I, $R^1$ is preferably a substituted or unsubstituted aliphatic group. Among substituted aliphatic groups, preferred substituent is hydroxyl. More preferably $R^1$ is an unsubstituted aliphatic group; more preferably, $R^1$ is an unsubstituted alkyl group. Preferably, $R^1$ is a linear alkyl group with 9-22 carbon atoms, or 9-18 carbon atoms, or 9-16 carbon atoms, or 10-17 carbon atoms, or 11-17 carbon atoms, or 11-15 carbon atoms, or 10-14 carbon atoms, or 11-13 carbon atoms. In some embodiments, $R^1$ is $CH_3$—$(CH_2)_{11}$—$CH_2$— or $CH_3$—$(CH_2)_9$—$CH_2$—. In some embodiments, $R^1$ is $CH_3$—$(CH_2)_{11}$—$CH_2$—.

In some embodiments (when n is not 0), $X^1$ is NH. In some embodiments, $X^2$ is NH.

In some embodiments, n is 0 or 1, 2, 3, 4 or 5. In some embodiments, n is 0 or 1. In some embodiments, n is 1. In some embodiments, n is 0.

In some embodiments, n is not 0, $R^2$ has 20 or fewer atoms; preferably 15 or fewer. Preferably, if $R^2$ is not hydrogen, then $R^2$ contains one or more carbon atom. Preferably, $R^2$ is either hydrogen or an unsubstituted hydrocarbon group; more preferably, $R^2$ is either hydrogen, an unsubstituted alkyl group, or an alkyl group whose only substituent is an unsubstituted aromatic hydrocarbon group. Among unsubstituted alkyl groups, preferred is methyl. Among alkyl groups whose only substituent is an unsubstituted aromatic hydrocarbon group, preferred is $-CH_2-(C_6H_5)$, where $-(C_6H_5)$ is a benzene ring. Preferably, $R^2$ represents a side chain of a naturally occurring amino acid.

In some embodiments, $R^3$ has a number-average molecular weight of 600-5000 Daltons, preferably 800-3000 Daltons. Preferably, the group $R^3$ is either a statistical copolymer of (II) and (III) or a block copolymer of (II) and (III); more preferably the group $R^3$ is a statistical copolymer of (II) and (III). Preferably, $-R^3$ has the structure $-R^4-CH_3$, where $R^4$ is a polymeric group comprising polymerized units of structure (II) and structure (III). Preferably, $R^4$ has no other polymerized units in addition to structure (II) and (III).

It is useful to characterize the mole ratio (herein the "PO/EO ratio") of units of structure (II) to units of structure (III). Preferably, the PO/EO ratio is 0.01:1 to 2:1; more preferably 0.05:1 to 1:1, in particular 0.1:1 to 0.5:1. The term, "PO", as used herein, means a structure (II) unit and the term, "EO", as used herein, means a structure (III) unit.

In some embodiments, $R^1$ is $CH_3-(CH_2)_{11}-CH_2-$, n is 0, $X^2$ is NH, and $R^3$ is a copolymer of PO and EO units capped with $CH_3$ with an approximate number-average molecular weight of 1000 and ratio of PO to EO of about 3:19.

In some embodiments, the polyalkoxy fatty acyl surfactant of formula I has no ionic groups.

In some embodiments, the polyalkoxy fatty acyl surfactant of formula I is selected from the group consisting of 12FM1000, FM1000, 16FM1000, 18FM1000, and mixtures thereof. In some embodiments, the polyalkoxy fatty acyl surfactant of formula I is selected from the group consisting of 12FM1000, FM1000, 16FM1000, and mixtures thereof. In some embodiments, the polyalkoxy fatty acyl surfactant of formula I is selected from the group consisting of 12FM1000, FM1000, and mixtures thereof. In some embodiments, the polyalkoxy fatty acyl surfactant of formula I is selected from the group consisting of FM1000, 16FM1000, and mixtures thereof. In some embodiments, the polyalkoxy fatty acyl surfactant of formula I is FM1000.

The polyalkoxy fatty acyl surfactant of formula I may be made by a method disclosed in WO2017/044366 which is incorporated herein by reference in its entirety for all purposes.

The polyalkoxy fatty acyl surfactant of formula I may be made by any suitable methods. A preferred method is to react a compound having structure $NH_2-R^3$ with a compound selected from compounds of structure V

V

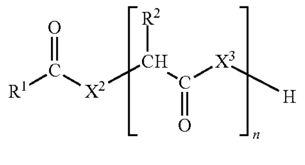

and compounds of structure VI

VI

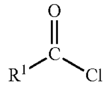

where $X^3$ is O, S, or NH. Preferences for $R^1$, $X^2$, $R^2$, $R^3$, and n are the same as those described above. Preferably, $X^3$ is O.

A more preferred method of making some embodiments of the polyalkoxy fatty acyl surfactant of formula I is as follows. In a first step, an acyl chloride is reacted with an amino acid to form a carboxyl-functional fatty amide as follows:

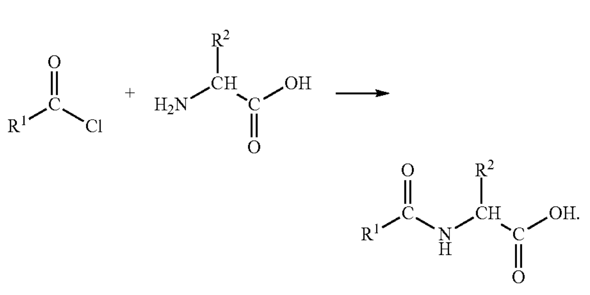

Then, in a second step, the carboxyl-functional fatty amide is reacted with an amine-terminated polyalkoxy compound, as follows:

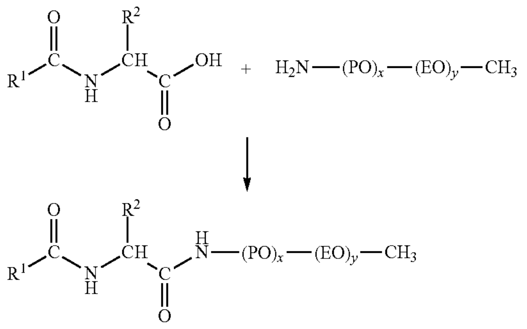

where PO is structure (II) and EO is structure (III).

Preferred proteins to be included in the present disclosure are selected from the group consisting of monoclonal antibodies, growth factors, insulins, immunoglobulins, polyclonal antibodies, antibody-drug conjugates, bispecific antibodies, trispecific antibodies, hormones, enzymes, polypeptides, fusions of peptides, glycosylated proteins, antigens, antigen subunits, and combinations thereof. Preferred proteins have therapeutic efficacy to treat a disease or medical condition or to function as vaccines. Examples of therapeutic proteins are immunoglobulin G (IgG), adalimumab, interferon alfa, bevacizumab, human growth hormone, rituximab, human serum albumin, insulin, erythropoietin alpha, pembrolizumab, etanercept, filgrastim, nivolumab, trastuzumab, durvalumab, interleukin-2, infliximab, chorionic gonadotropin, avelumab, denosumab, ranibizumab, aflibercept, tremelimumab, factor viii, interferon beta, ipilimumab, atezolizumab, abatacept, tocilizumab, ustekinumab, pegfilgrastim, secukinumab, streptokinase, cetuximab, omalizumab, ramucirumab, urokinase, certolizumab pegol, dupilumab, genolimzumab, aldesleukin, molgramostim, peginterferon alfa-2b, tislelizumab, follitropin alfa, gevokizumab, golimumab, spartalizumab, canakinumab, foralumab, varlilumab, nimotuzumab, erythropoietin beta, evolocumab, pegargiminase, bermekimab, carotuximab, daratumumab, eculizumab, ontuxizumab, adalimumab, camrelizumab, enoblituzumab, interleukin-12, lirilumab, panitumumab, gatipotuzumab, relatlimab, andecaliximab, belimumab, cabiralizumab, isactuzumab govitecan, monalizumab, pancreatin, pertuzumab, toripalimab, inebilizumab, ofatumumab, pepinemab, sintilimab, alirocumab, milatuzumab, nidanilimab, sotatercept, vedolizumab, veltuzumab, bevacizumab beta, isatuximab, orlotamab, tisotumab vedotin, benralizumab, cosibelimab, emactuzumab, ganitumab, narsoplimab, pidilizumab, sarilumab, trastuzumab emtansine, anetumab ravtansine, bertilimumab, blinatumomab, guselkumab, ixekizumab, mepolizumab, obinutuzumab, ublituximab, alemtuzumab, emibetuzumab, ficlatuzumab, ifabotuzumab, mirikizumab, natalizumab, racotumomab, siltuximab, timigutuzumab, trastuzumab deruxtecan, bimekizumab, brodalumab, cetrelimab, farletuzumab, opinercept, rilonacept, tomuzotuximab, urelumab, ascrinvacumab, brolucizumab, clazakizumab, cusatuzumab, dalotuzumab, ianalumab, itolizumab, and margetuximab. Also contemplated are proteins that can be used as medical diagnostics or have a beneficial effect on a food composition, or be incorporated in a cleaning composition or a coatings formulation. In some embodiments, the protein is an immunoglobulin. In some embodiments, the protein is an immunoglobulin G (IgG). In some embodiments, the protein is a bovine immunoglobulin G.

The term "aqueous solution", as used herein, means a solution in which the solvent comprises at least 90 wt % of water based on the total weight of the solvent. In some embodiments, the solvent further comprises an organic solvent such as acetone, ethanol, DMSO (dimethyl sulfoxide) and 2-butanone. In some embodiments, the solvent comprises, consists essentially of or consists of water and an organic solvent. In some embodiments, the solvent comprises at least 92 wt %, or at least 94 wt %, or at least 96 wt %, or at least 98 wt %, or at least 99 wt % of water based on the total weight of the solvent. In some embodiments, the solvent consists essentially of or consists of water. In some embodiments, the solvent is water. In some embodiments, the aqueous solution is substantially free of an organic solvent. In some embodiments, the liquid medium of the aqueous solution consists essentially of or consists of water.

The aqueous solution optionally comprises one or more additional ingredients. Additional ingredients are compounds other than water, proteins, and polyalkoxy fatty acyl surfactant of formula I. Preferred additional ingredients are sugars, sugar alcohols, salts, buffers, amino acids or salts of amino acids, or mixtures thereof. When such additional ingredients are present, preferably the total amount of all additional ingredients is no more than 300 mg/ml, or no more than 250 mg/ml, or no more than 200 mg/ml, or no more than 150 mg/ml, or no more than 100 mg/ml, or no more than 80 mg/ml, or no more than 60 mg/ml, or no more than 40 mg/ml, or no more than 30 mg/ml, or no more than 20 mg/ml, or no more than 10 mg/ml, based on the total volume of the aqueous solution.

For inclusion in the aqueous solution, preferred sugars are sucrose, glucose, mannose, trehalose, maltose, dextrose or dextran, or mixtures thereof. Preferred sugar alcohols for inclusion in the aqueous solution are sorbitol, mannitol or xylitol.

For inclusion in the aqueous solution, preferred salts have cations chosen from hydrogen, sodium, potassium, magnesium, calcium or ammonium, or mixtures thereof. Preferred salts have anions chosen from fluoride, chloride, bromide, iodide, phosphate, carbonate, acetate, citrate or sulfate, or mixtures thereof. Preferred buffers have cations chosen from hydrogen, sodium, potassium, magnesium, calcium or ammonium, or mixtures thereof.

For inclusion in the aqueous solution, preferred amino acids and salts thereof are selected from the group consisting of lysine, glycine, proline, arginine, histidine, and mixtures thereof and salts thereof.

In some embodiments, the aqueous solution is substantially free of other surfactant. The term "other surfactant", as used herein, means a surfactant different from the polyalkoxy fatty acyl surfactant of formula I. In some embodiments, the other surfactant is selected from the group consisting of polysorbates, poloxamers, and mixtures thereof. In some embodiments, the aqueous solution is substantially free of a polysorbate surfactant. In some embodiments, the aqueous solution is substantially free of a poloxamer surfactant. In some embodiments, the concentration of the other surfactant in the aqueous solution is no more than 0.01 mg/ml, or no more than 0.005 mg/ml, or no more than 0.002 mg/ml, or no more than 0.001 mg/ml, or no more than 0.0005 mg/ml, or no more than 0.0002 mg/ml, or no more than 0.0001 mg/ml, based on the total volume of the aqueous solution. In some embodiments, the polyalkoxy fatty acyl surfactant of formula I is the only surfactant present in the aqueous solution.

In some embodiments, the bioprocess in step (b) is filtration, that is, in step (b), the aqueous solution provided in step (a) is filtered to form an aqueous solution of filtrate. In such step or process, the aqueous solution passes through the filter to remove at least a portion of protein contaminants (e.g., host cell proteins, nucleic acids, protein aggregates, etc.). The protein and the polyalkoxy fatty acyl surfactant of formula I in the aqueous solution pass through the filter together to form the filtrate while protein contaminants are retained by the filter.

In some embodiments, the filter is selected from the group consisting of PVDF filter, PES filter, polypropylene filter, cellulose filter, nylon filter, and combinations thereof. In some embodiments, the filter is a PVDF filter. In some embodiments, the filter is a PES filter. Typically the filter comprises a separation membrane. The term "separation membrane", as used herein, means a porous membrane that is used in the filtering process to separate components in the aqueous solution based on their molecular weight or size. The term "PVDF filter", as used herein, means a filter having a separation membrane made of polyvinyledene fluoride (PVDF). The term "PES filter", as used herein, means a filter having a separation membrane made of polyethersulfone (PES). The term "polypropylene filter", as used herein, means a filter having a separation membrane made of polypropylene. The term "cellulose filter", as used herein, means a filter having a separation membrane made of cellulose. The term "nylon filter", as used herein, means a filter having a separation membrane made of nylon.

In some embodiments, the filter or the separation membrane therein has a pore size of from about 0.1 μm to about 1 μm, or from about 0.1 μm to about 0.5 μm. In some embodiments, the filter or the separation membrane therein has a pore size of about 0.2 μm. In some embodiments, the filtering process is conducted under room temperature. In some embodiments, the filtering process excludes ultrafiltration and/or diafiltration.

It was discovered that polyalkoxy fatty acyl surfactant of formula I can effectively prevent proteins from being absorbed or lost on the separation membrane. In addition, the polyalkoxy fatty acyl surfactant of formula I absorption or loss on the separation membrane is also small or minimal. In some embodiments, at least 60%, or at least 70%, or at least 75%, or at least 80%, or at least 85%, or at least 90%, or at least 92%, or at least 95%, or at least 98%, or at least 99% of the polyalkoxy fatty acyl surfactant of formula I pass through the filter, based on the total weight of the polyalkoxy fatty acyl surfactant of formula I in the aqueous solution fed to the filter for filtration.

In some embodiments, at least 60%, or at least 70%, or at least 75%, or at least 80%, or at least 85%, or at least 90%, or at least 92%, or at least 95%, or at least 98%, or at least 99% of the protein pass through the filter, based on the total weight of the protein in the aqueous solution fed to the filter for filtration.

In some embodiments, the surfactant/protein concentration ratio in the aqueous solution provided in step (a) is substantially the same as the surfactant/protein concentration ratio in the aqueous solution of filtrate, that is, the surfactant/protein concentration ratio in the aqueous solution is substantially constant when passing through the filter. In some embodiments, the surfactant/protein concentration ratio in the aqueous solution of filtrate is within the range of ±5%, or ±10%, or ±15%, or ±20% from the surfactant/protein concentration ratio in the aqueous solution provided in step (a).

The polyalkoxy fatty acyl surfactant of formula I is a mixture of polymer components with different molecular weights. Typically, the composition (polymer components and their respective concentrations in the mixture) of the polyalkoxy fatty acyl surfactant of formula I in the aqueous solution provided in step (a) is substantially the same as the composition of the polyalkoxy fatty acyl surfactant of formula I in the aqueous solution of filtrate, that is, the composition of the polyalkoxy fatty acyl surfactant of formula I in the aqueous solution remains substantially the same when passing through the filter.

In some embodiments, the bioprocess in step (b) is chromatography, that is, in step (b), the aqueous solution provided in step (a) is passed through a chromatography resin (stationary phase) contained in a chromatography column so that at least a portion of protein contaminants (e.g., host cell proteins, nucleic acids, protein aggregates, etc.) can be separated from the protein. In some embodiments, the protein is retained in the chromatography column while the protein contaminants pass through the chromatography column. In such embodiments, after chromatography, a recovery aqueous solution comprising the polyalkoxy fatty acyl surfactant of formula I can be used to recover or remove the retained protein from the chromatography column. In some embodiments, the recovery aqueous solution is a buffer solution.

In some embodiments, the protein contaminants are retained in the chromatography column while the protein and the polyalkoxy fatty acyl surfactant of formula I in the aqueous solution pass through the chromatography column. In some embodiments, the chromatography process is conducted under room temperature.

During the chromatography process, the polyalkoxy fatty acyl surfactant of formula I in the aqueous solution passes through the chromatography column. The polyalkoxy fatty acyl surfactant of formula I absorption or loss on the chromatography resin is small or minimal. In some embodiments, at least 60%, or at least 70%, or at least 75%, or at least 80%, or at least 85%, or at least 90%, or at least 92%, or at least 95%, or at least 98%, or at least 99% of the polyalkoxy fatty acyl surfactant of formula I pass through the chromatography column, based on the total weight of the polyalkoxy fatty acyl surfactant of formula I in the aqueous solution fed to the chromatography column.

Typically, the composition of the polyalkoxy fatty acyl surfactant of formula I in the aqueous solution provided in step (a) is substantially the same as the composition of the polyalkoxy fatty acyl surfactant of formula I in the aqueous solution passed through the chromatography column (i.e., eluate), that is, the composition of the polyalkoxy fatty acyl surfactant of formula I in the aqueous solution remains substantially the same when passing through the chromatography column.

The chromatography column comprises a chromatography resin (stationary phase) contained therein. In some embodiments, the chromatography resin is selected from the group consisting of sulfopropyl-functionalized cross-linked agarose, Protein A, quaternary ammonium-functionalized cross-linked agarose, hydrophobic interaction chromatography resins, and combinations thereof. A person skilled in the art appreciates that Protein A is a 49 kDa surface protein originally found in the cell wall of the bacteria *Staphylococcus aureus*. Examples of hydrophobic interaction chromatography resins include agarose with butyl substituents. In some embodiments, the chromatography resin is sulfopropyl-functionalized cross-linked agarose. In some embodiments, the chromatography resin is Protein A. In some embodiments, the chromatography resin is quaternary ammonium-functionalized cross-linked agarose.

In some embodiments, the bioprocess is transportation, that is, the bioprocess comprises transporting the aqueous solution in a container or through a conduit. In some embodiments, the polyalkoxy fatty acyl surfactant of formula I is selected from the group consisting of 12FM1000, FM1000, and mixtures thereof. In some embodiments, the polyalkoxy fatty acyl surfactant of formula I is FM1000. In some embodiments, the concentration of the polyalkoxy fatty acyl surfactant of formula I in the aqueous solution is from about 0.01 mg/ml to about 0.1 mg/ml, or from about 0.02 mg/ml to about 0.08 mg/ml, or from about 0.02 mg/ml to about 0.06 mg/ml, or from about 0.03 mg/ml to about 0.05 mg/ml, based on the total volume of the aqueous solution. In some embodiments, the concentration of the polyalkoxy fatty acyl surfactant of formula I in the aqueous solution is about 0.03 mg/ml based on the total volume of the aqueous solution.

It was discovered that polyalkoxy fatty acyl surfactant of formula I can effectively reduce aggregation of the protein in the aqueous solution during transportation. In some embodiments, the aqueous solution at the end of transportation comprises at least 80 wt % monomer protein, or at least 85 wt % monomer protein, or at least 90 wt % monomer protein, or at least 92 wt % monomer protein, or at least 94 wt % monomer protein, or at least 96 wt % monomer protein, or at least 98 wt % monomer protein, or at least 99 wt % monomer protein based on the total weight of the protein in the aqueous solution.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

Proteins are known to adsorb onto interfaces between water and air, oil, and solid surfaces, which often leads to aggregation and denaturation. Furthermore, agitation, a common occurrence during transport, can exacerbate these harmful effects. Some methods to stabilize these therapeutic proteins include use of excipients such as sugars, salts, amino acids, and surfactants. Surfactants are particularly useful to stabilize and protect the protein in solution through two mechanisms: (1) by out-competing the protein for space on the surface where the protein can denature and aggregate, known as competitive adsorption, and (2) by preferential association, where the surfactant directly interacts with the protein to stabilize the protein structure or to prevent protein-protein interactions that can cause aggregation.

Without wishing to be bound by the theory, it is believed that both of these mechanisms play a role in the stabilization, but generally, the first is considered the primary. Current surfactants on the market used for protein stabilization, such as polysorbates 20 and 80, decrease protein aggregation compared to formulations without such surfactants. Compared to polysorbates 20 and 80, 14FM1000 leads to a decreased rate of growth of immunoglobulin G (IgG) aggregates when protein-surfactant solutions are held isothermally at 65° C. Without wishing to be bound by the theory, it is believed that the success of 14FM1000 is likely due to its ability to move and adsorb quickly to different interfaces such as aqueous-air and aqueous-oil as shown by dynamic surface tension (DST) measurements.

Six FM1000 derivatives with hydrophobic tail lengths ranging from 8 to 18 carbons were synthesized and studied to understand their protein stabilization abilities and to discern the surfactant structural properties that lead to the changes in protein stabilization efficacy. It was found through experiments that hydrophobic tail length significantly impacts the ability of a surfactant to stabilize a model protein therapeutic, IgG. The hydrophobic tail length affects the kinetics and reversibility of surfactant adsorption. Mid-length hydrophobic tails lengths such as 14 carbons (i.e., 14FM1000) have the fastest and largest decrease in surface tension and the most reversible adsorption. These fast dynamics correlates with a surfactant's ability to stabilize IgG, with 14FM1000 minimizing aggregation the most. This disclosure elucidates the structure-function relationship between surfactant hydrophobic tail length and protein stabilization.

Materials

Myristoyl chloride, Amberlite IR-120 strongly acidic ion exchange resin hydrogen form, and carbonyldiimidazole were purchased from Sigma Aldrich (St. Louis, MO). Amberlite IRN-78 cationic type (OH−) ion exchange resin was purchased from Thermo Fisher Scientific (Waltham, MA). N-Hydroxysuccinimide was purchased from Acros Organics (Fair Lawn, NJ). L-phenylalanine was purchased from TCI chemicals (Portland, OR). Jeffamine M1000 was obtained from Huntsman (The Woodlands, TX). Polysorbate 80 and polysorbate 20 were purchased from Sigma. All chemicals were used as received without further purification.

Silicone slabs (Dow Corning C6-150) were supplied by DuPont. IV bags were obtained from Baxter Healthcare Corp., cut open and emptied from the existing saline solution, washed with MilliQ water, and dried. Slabs of polyvinyledene fluoride (PVDF), polytetrafluoroethylene (PTFE), polyethersulfone (PES), and polyethylene (PE) were all obtained from Goodfellow Corp. with a thickness of 0.5 mm and sizes ranging between 150×150 mm and 300×300 mm. All surfaces were cut into 3.5×1 cm pieces before immersing them into different solutions.

PVDF filters were obtained from Fisher Scientific (Fisherbrand, 33 mm diameter, 0.2 μm) while PES filters were obtained from Millipore Sigma (Millex-GP, 33 mm diameter, 0.22 μm). Chromatography columns were obtained from Cytiva, including the sulfopropyl-functionalized cross-linked agarose column and the Protein A columns (GE Healthcare), all in 1 mL capacity.

Water was MilliQ grade. Industrial grade bovine IgG (immunoglobulin G) was purchased from MP Biomedicals (Santa Ana, CA). Bovine IgG was dissolved at 40 mg/mL in 0.9 wt % saline, filtered through a 0.2 μm PVDF filter and diluted down to the relevant concentration.

Synthesis of FM1000 Derivative with 14 Carbon Hydrophobic Tail (FM1000 or 14FM1000):

Step 1: To a 500 mL round bottom flask equipped with a stirbar was added I-phenylalanine (0.0500 mol, 8.26 g), sodium hydroxide (0.0500 mol, 2.00 g) in DI (deionized) water (250 mL), and triethylamine (0.0540 mol, 7.56 mL). This was allowed to stir at RT (room temperature) for 1 minute until dissolved. Next, myristoyl chloride (0.0500 mol, 13.6 mL) was added slowly. The reaction mixture was allowed to stir for 1 hour at RT. Next, 5 mL of concentrated HCl were added slowly. The off-white precipitate that formed with addition of the acid was collected via suction filtration, washed with 500 mL of water and allowed to dry overnight. Next, the product was dissolved in 1500 mL of boiling ethyl acetate and dried over magnesium sulfate. The magnesium sulfate was filtered off and the ethyl acetate was removed via a rotary evaporator. Next, the product was dissolved in boiling hexanes, cooled slowly in the freezer during which a white precipitate formed, and collected via suction filtration. Since an NMR showed myristic acid impurities, the product was again dissolved in boiling hexanes, cooled slowly in the freezer during which a white precipitate formed, and collected via suction filtration. The resulting white powder was dried in the vacuum desiccator overnight (7.9741 g, 43%).

Step 2: To a 25 mL round bottom flask equipped with a stir bar was added n-myristoyl phenylalanine (product from step 1) (0.00100 mol, 0.375 g) and DCM (dichloromethane, 10 mL). The round bottom flask was capped with a septum and purged with $N_2$. Next, CDI (1,1'-carbonyldiimidazole, 0.00120 mol, 0.194 g) was added to the reaction mixture, the septum was replaced, and the mixture was purged with $N_2$ again. The reaction mixture was then stirred at RT for 4 hours. Next, the Jeffamine M1000 (0.00120 mol, 1.17 g) was melted and added to the reaction mixture via a syringe. The reaction mixture was stirred at RT for 68 hours. Next, the DCM was evaporated via a rotary evaporator, and 150 mL of methanol was added along with the prewashed with methanol exchange resins, Amberlite IRN-78 cationic type (OH−) ion exchange resin and Amberlite IR-120 strongly acidic ion exchange resin hydrogen form. This mixture was stirred at RT for 2 hours. The resins were removed via vacuum filtration using a frit. The methanol was evaporated off the resulting solution from vacuum filtration. Next, the product was dissolved in 400 mL of 10% methanol/DCM and run through a $SiO_2$ plug. The filtrate was concentrated via a rotary evaporator yielding a white wax, which was dried in the vacuum oven at 60° C. overnight (1.6 g, 49%).

Shake Study

All samples were prepared in 0.9 wt % saline (9 g NaCl in 1000 mL MilliQ water) and contained 20 mg/mL IgG. A control sample was prepared without surfactant. Other samples containing 0.03 or 0.05 mg/mL of surfactant with different tail length were also prepared for the shake study. The surfactants were 8FM1000, 10FM1000, 12FM1000, 14FM1000, 16FM1000 and 18FM1000, wherein 8, 10, 12, 14, 16 and 18 means the surfactant tail length (number of carbon atoms) respectively. The term “tail length”, as used herein, means the length of $R^1$. For example, 14FM1000 has a 14-carbon hydrophobic tail length ($CH_3$—$(CH_2)_{11}$—$CH_2$—C(═O)).

IgG protein aggregation was induced using agitation. Samples were shaken at room temperature for 24 hours at 188 strokes/minute in quadruplet on a Thermo reciprocal shaker. Each sample for study was 0.7 mL in an approximately 1 mL, 8×43 mm glass vial (Kimble product number 60831 D-843) and capped with a Piercable TPE Lyo Capcluster-96 (Micronic, Aston, PA) stopper. Vials were arrayed in a 96-well layout on a custom aluminum holder. After shaking, samples were analyzed via dynamic light scattering (DLS) on a Wyatt DynaPro II instrument (Wyatt Technology, Santa Barbara, CA) to determine the efficacy of surfactants at preventing agitation-induced aggregation. In addition, the same samples were analyzed via DLS prior to shaking as “no-shake” controls (i.e., “0 hour shake”). Each well was scanned 5 times with 5 seconds per acquisition. Regularization fitting was used to determine IgG population size and hydrodynamic radius. Populations above 10 nm were considered aggregated IgG and therefore quantified by mass percent by assuming a Rayleigh sphere to convert from intensity percent to mass percent.

Figure 2:
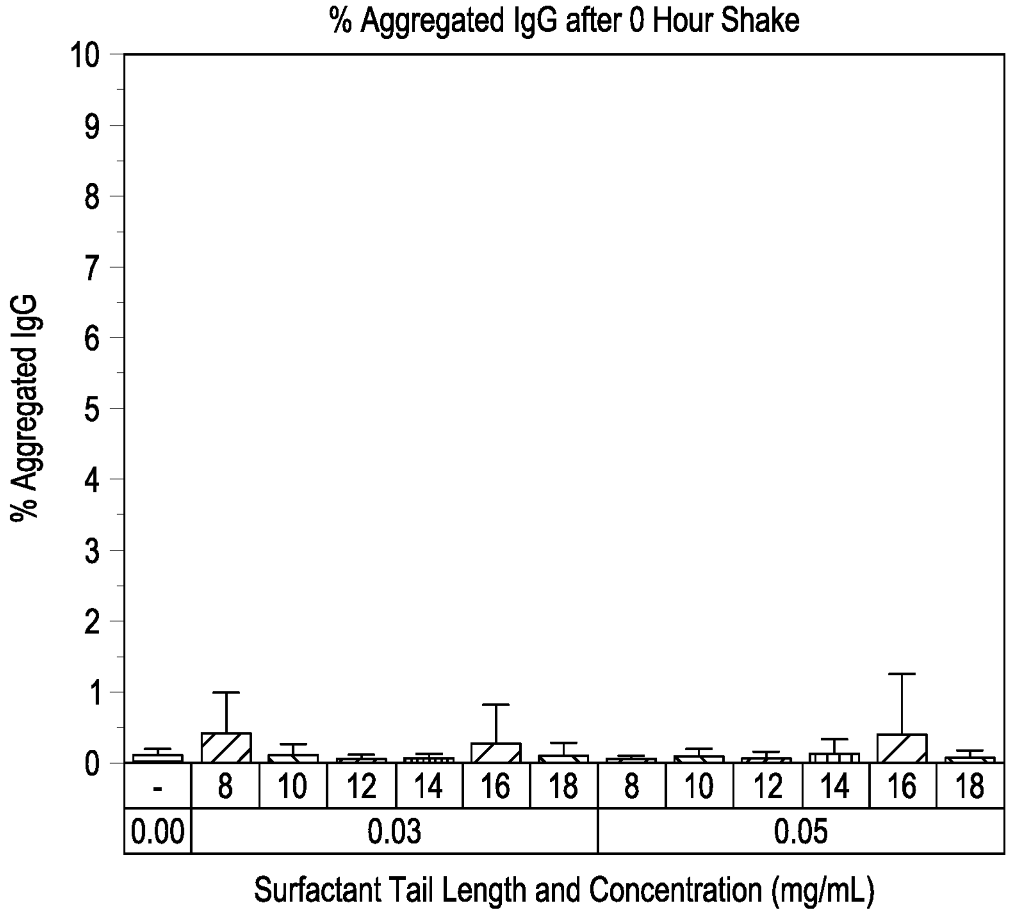
FIG. 2 is a graph showing percent aggregation of IgG (20 mg/mL) by different surfactant tail lengths at 0.03 mg/mL surfactant and 0.05 mg/mL surfactant in saline before shaking as measured by DLS.

The shake study is used to understand the surfactants' abilities to stabilize protein, as shaking accelerates destabilization through constant fluctuations in hydrophobic surfaces. Additionally, agitation resembles transportation conditions that increase IgG aggregation. In FIGS. 1 and 2, the leftmost bar represents the control sample containing no surfactant. FIG. 1 shows IgG aggregation after 24 hour shake, and FIG. 2 shows IgG aggregation before shaking. As shown by FIG. 2, in the no-shake controls, there is essentially 0% aggregation of IgG for all surfactants at the two concentrations studied. FIG. 1 demonstrated that 14FM1000 can effectively prevent IgG protein aggregation at the concentration of 0.03 mg/ml and 0.05 mg/ml based on the total volume of the aqueous solution. FIG. 1 also demonstrated that 12FM1000 can effectively prevent IgG protein aggregation at the concentration of 0.05 mg/ml based on the total volume of the aqueous solution.

It was discovered that generally mid-tail lengths prevented IgG aggregation the most, and shorter and longer tail length exhibited more IgG aggregation. When comparing IgG aggregation between the 0.03 mg/mL and 0.05 mg/mL surfactant concentrations, it was discovered that at the higher concentration of surfactant (0.05 mg/mL), 12FM1000 also had approximately 0% aggregation, but at the lower concentration of 0.03 mg/mL some aggregation (1-2%) was observed. The 8FM1000 and 10FM1000 surfactant samples had a large amount of aggregation (4-7%) at 0.03 mg/mL. At a higher concentration of 0.05 mg/mL, 8FM1000 had approximately the same amount of aggregation as it did at the lower concentration, but 10FM1000 had less aggregation (2-3%). This decrease in IgG aggregation with increasing concentration for 10FM1000 is similar to the trend seen when increasing the concentration of 12FM1000 as well. Both 16FM1000 and 18FM1000 had about 2-3% of aggregation that did not change significantly between the two concentrations studied.

Dynamic Surface Tension Measurements

All samples were prepared in 0.9 wt % saline (9 g NaCl in 1000 mL MilliQ water). The surfactants were 8FM1000, 10FM1000, 12FM1000, 14FM1000, 16FM1000 and 18FM1000 respectively, and the protein was IgG. Seven samples were prepared, one containing 10 mg/mL IgG in 0.9% saline, and the other six containing each kind of surfactant respectively at the concentration of 0.05 mg/mL in 0.9% saline.

Surface tension measurements were taken at RT on a Teclis Tracker pendant drop tensiometer (Teclis Scientific, Civrieux d'Azergues, France). A 25 ml cuvette was filled with sample. An 18-gauge J-shaped needle was used to create an air bubble. The drop was kept at a constant area using a feedback controller on the instrument. Surface tension was calculated by fitting the air bubble outline to the Laplace equation. Surface tension of a sample was monitored for 3000 seconds (12FM1000, 14FM1000, 16FM1000, 18FM1000, and IgG) or 6000 seconds (8FM1000 and 10FM1000) in triplicate. Initially, measurements were taken every 0.1 seconds. After 10 seconds, measurements were taken every 1 second.

Figure 3A:
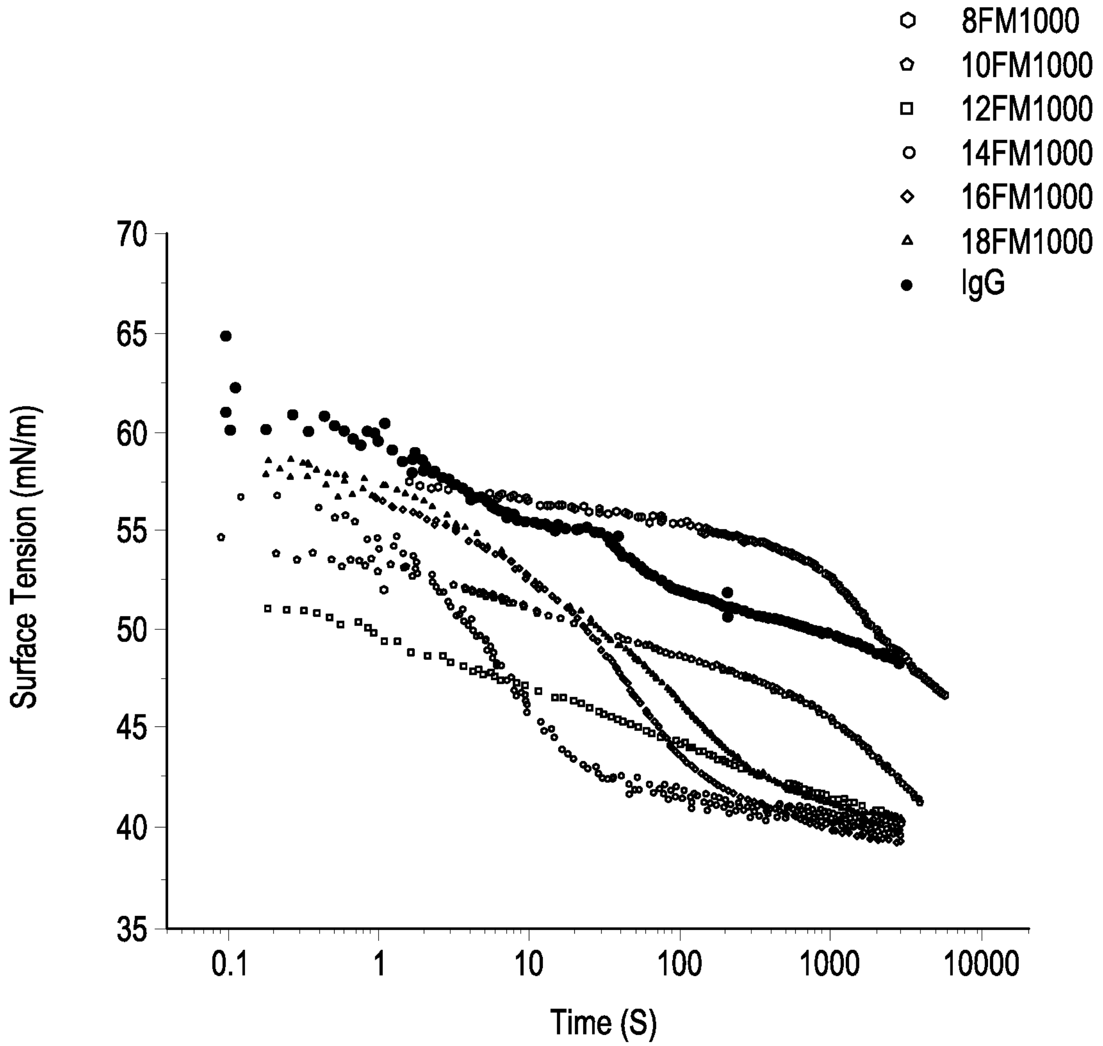
FIG. 3A shows representative DST traces for the six FM1000 derivatives studied and IgG.

Dynamic surface tension (DST) measurements are useful for understanding the kinetics of material adsorption and rearrangement at the interface. DST at an air/water interface was measured for each surfactant at 0.05 mg/mL and for IgG at 10 mg/mL (see FIG. 3A). Each DST curve was fit to a double exponential decay function to qualitatively represent the adsorption and rearrangement dynamics at the interface (Equation 1). $\sigma(t)$ is the surface tension at time t and $\sigma_{eq}$ is the surface tension at equilibrium or after infinite time. In addition, $\tau_1$ is the characteristic time of the faster decay and $\theta_1$ is the decrease in surface tension due to the first decay. $\tau_2$ and $\theta_2$ correspond to that of the slower decay.

$$\sigma(t)=\theta_1 e^{-t/\tau_1}+\theta_2 e^{-t/\tau_2}+\sigma_{eq} \qquad \text{Equation 1}$$

It is believed that polyalkoxy fatty acyl surfactant of formula I undergoes the hydrophilic head (—$R^3$) and hydrophobic tail (—$R^1$) rearrangement and adsorption onto surfaces. Assuming that the polyalkoxy fatty acyl surfactant of formula I has two types of surface tension decay, initial adsorption and some form of conformational adjustment, which is probable due to its polymeric hydrophilic head (—$R^3$), it is believed that the first decay corresponds to initial adsorption of the surfactant to the surface ($\tau_1$, $\theta_1$) and the second decay corresponds to the conformational changes of the surfactant molecules to their equilibrium orientation ($\tau_2$, $\theta_2$). There can be conformational adjustments of the polymeric hydrophilic head and the hydrocarbon hydrophobic tail (—$R^1$).

Figure 3B:
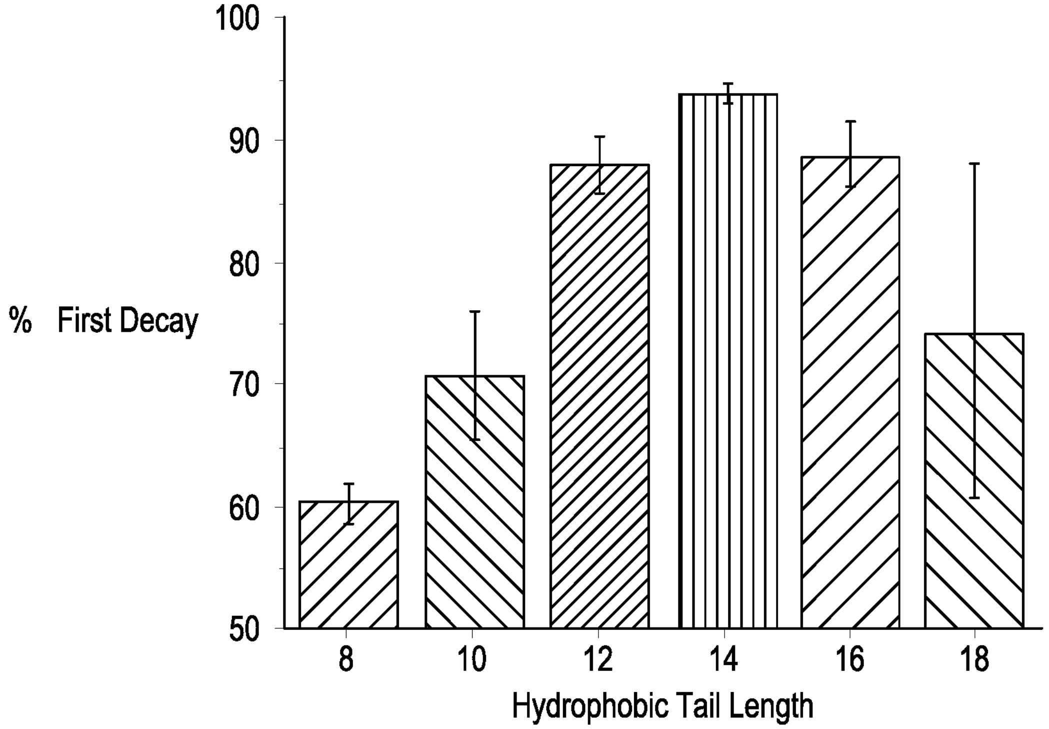
FIG. 3B shows percent of surface tension decrease due to the first decay relative to the total surface tension decrease.
Figure 3C:
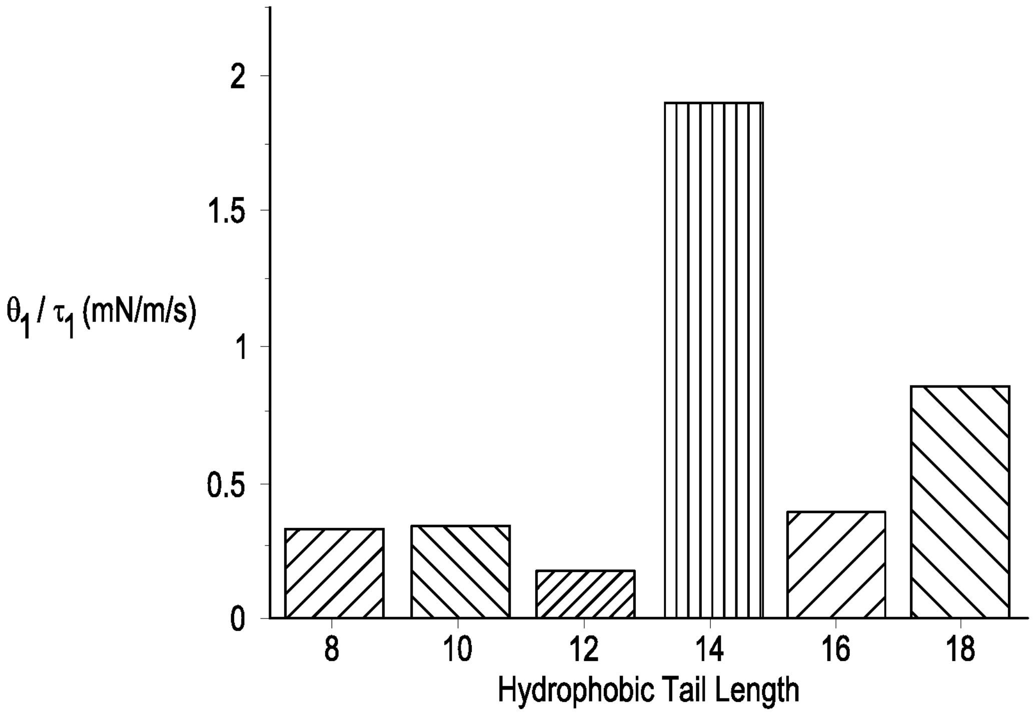
FIG. 3C shows surface tension decrease during the first decay normalized by the characteristic time for the first decay.

It was discovered that 14FM1000 decreased the largest percentage of its surface tension in the first decay (see FIG. 3B). Relative to 14FM1000, as the tail length increases or decreases, the percent of surface tension reduction due to the first decay decreases. This indicates that the tail length of 14FM1000 allows for maximum initial adsorption relative to other surfactants. Furthermore, by normalizing the initial decrease by the time-constant for that decrease, as seen in FIG. 3C, 14FM1000 decreased surface tension the most in the least amount of time. Therefore, 14FM1000 is comparatively much faster at reaching the surface first.

Figure 3D:
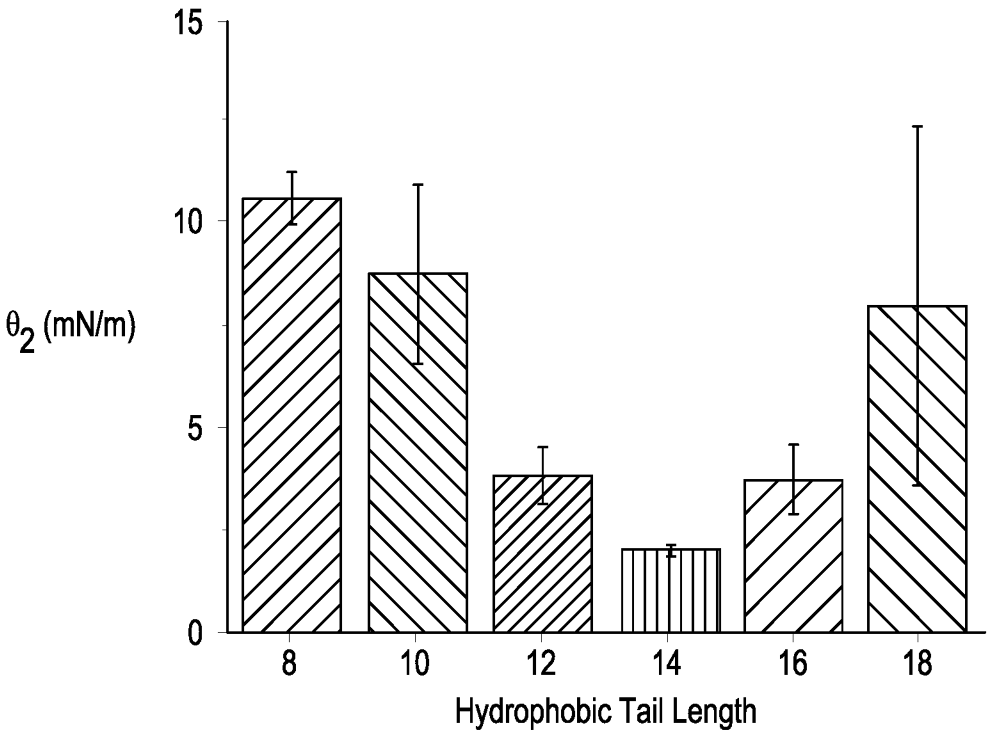
FIG. 3D shows decrease in surface tension due to the second decay.
Figure 3E:
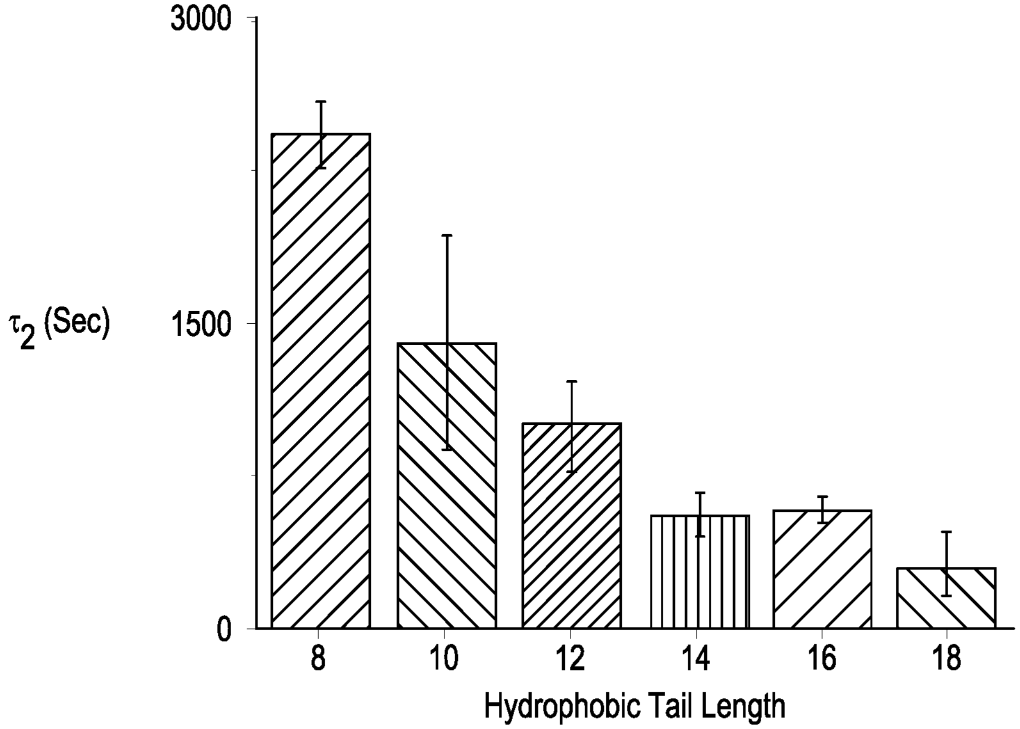
FIG. 3E shows characteristic time for second decay.

Interestingly, the opposite trend occurs when looking at the amount of surface tension decrease due to the second decay: shorter and longer tails (comparing with 14FM1000) both decreased surface tension the most during the second decay (see FIG. 3D). Without wishing to be bound by the theory, this trend could potentially be due to longer and shorter tail lengths needing more conformational changes to reach equilibrium. For longer tails, the hydrophobic tail must rearrange so that most of it can be adsorbed in the equilibrium orientation. For all surfactants studied, the hydrophilic head potentially could adsorb either through the PEO (polyethylene oxide), PPO (polypropylene oxide) or phenylalanine regions causing a large decrease in surface tension. This hydrophilic head adsorption might be more prominent for shorter tails as the tail itself is not as hydrophobic. Without wishing to be bound by the theory, the quick adsorption of 14FM1000 can be due to that the hydrophobic tail is short enough that it does not have to rearrange significantly, but it is also hydrophobic enough that PEO, PPO or phenylalanine do not adsorb significantly at equilibrium. This leads to very minimal surface tension decrease due to rearrangement. The characteristic time for the second decay ($\tau_2$) decreases as the hydrophobic tail length increases (see FIG. 3E). Without wishing to be bound by the theory, this is because of the stronger thermodynamic drive for the more hydrophobic tail to rearrange and minimize its (higher) energy. The trend in the characteristic time for the second decay might further be impacted by the polymeric hydrophilic head rearrangement that is likely more important for less hydrophobic (smaller) tails. Since a polymeric hydrophilic head takes significantly longer to change conformations compared to the tail due to its high molecular weight, this time for rearrangement could impact the trend in tau 2. FIG. 3 demonstrated that 14FM1000 has the ideal hydrophobic tail length having both a rapid and large initial decrease in surface tension.

It is believed that the amount and how fast 14FM1000 adsorbs promotes its ability to outcompete IgG for surface adsorption, ultimately preventing IgG aggregation. Moreover, the DST and aggregation data combined indicate that longer and shorter tails (comparing with 14FM1000) prevent less IgG aggregation since they adsorb to the surface slower allowing time for IgG to adsorb and aggregate on hydrophobic surfaces. It is also believed that these quick adsorption dynamics are why 14FM1000 outperformed polysorbates 20 and 80 in preventing protein aggregation. It is further believed that even if a polyalkoxy fatty acyl surfactant of formula I can displace IgG, if it is able to get to the surface quicker to do this, the surfactant can displace more protein thus preventing more aggregation. Interestingly, 8FM1000 is the only surfactant that has higher surface tension values than IgG for all times measured after approximately 5 seconds (see FIG. 3A). This indicates that 8FM1000 does not coat the surface as quickly or as well as IgG does, possibly indicative of why 8FM1000 does not prevent IgG aggregation well at either concentration studied.

Quartz Crystal Microbalance with Dissipation Study

All samples were prepared in 0.9 wt % saline solution (9 g NaCl in 1000 mL MilliQ water). The surfactants were 8FM1000, 10FM1000, 12FM1000, 14FM1000, 16FM1000 and 18FM1000 respectively, and the protein was IgG. Sample solutions were prepared to have 0.05 mg/mL surfactant alone in saline, or have 1 mg/mL IgG alone in saline, or have a combination of 0.05 mg/mL surfactant and 1 mg/mL IgG in saline.

Quartz crystal microbalance with dissipation (QCM-D) measurements were taken on a QSense Analyzer (Biolin Scientific, Gothenberg, Sweden) using $SiO_2$-coated quartz crystals (model QSX 303). A sample solution was flowed over the quartz crystal at a rate of 150 μL/min until equilibrium was reached to determine the amount of material adsorbed. Next, a solution of 0.9 wt % saline was flowed over the quartz crystal at a rate of 150 μL/min until equilibrium was reached to determine how much surfactant and/or protein could be rinsed off after being adsorbed onto the crystal. The third harmonic frequency change was monitored to determine relative mass adsorbed following the Sauerbrey relationship, which postulates that mass adsorbed is proportional to the frequency change. The first 10 to 40 minutes after the surfactant alone or surfactant and IgG solution was started were averaged to determine the relative mass adsorbed. The percent rinsed off was determined by taking the relative mass adsorbed before the saline rinse and comparing it to the change in mass adsorbed averaged over 40 minutes of the saline rinse. Additionally, percent IgG adsorbed (FIG. 4C) was calculated by taking the difference between the average mass adsorbed over minutes 10 to 40 with and without IgG for each surfactant. All data was normalized to the average mass adsorbed for IgG alone sample (100 arbitrary units).

QCM-D is used to elucidate the IgG and surfactant mass adsorbed onto a solid hydrophobic surface by monitoring the change in resonance frequency of a silicon-coated quartz crystal. Rinse-off studies can further be used to understand if adsorption is reversible or irreversible, elucidating how surfactants and IgG interact with the surface. Sample solutions of 0.05 mg/mL surfactant alone were flowed over the crystal surface, and the resonance frequency change was measured over time. Generally, as the surfactant tail length increases, the mass of the surfactant adsorbed increases (see FIG. 4A).

Figure 4A:
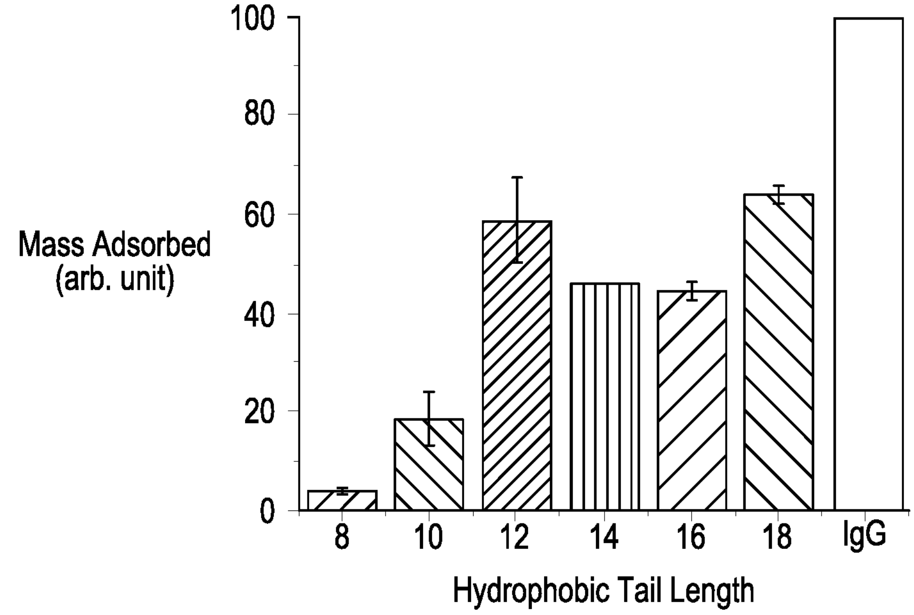
FIG. 4A shows relative mass of surfactant alone or IgG alone adsorbed.
Figure 4B:
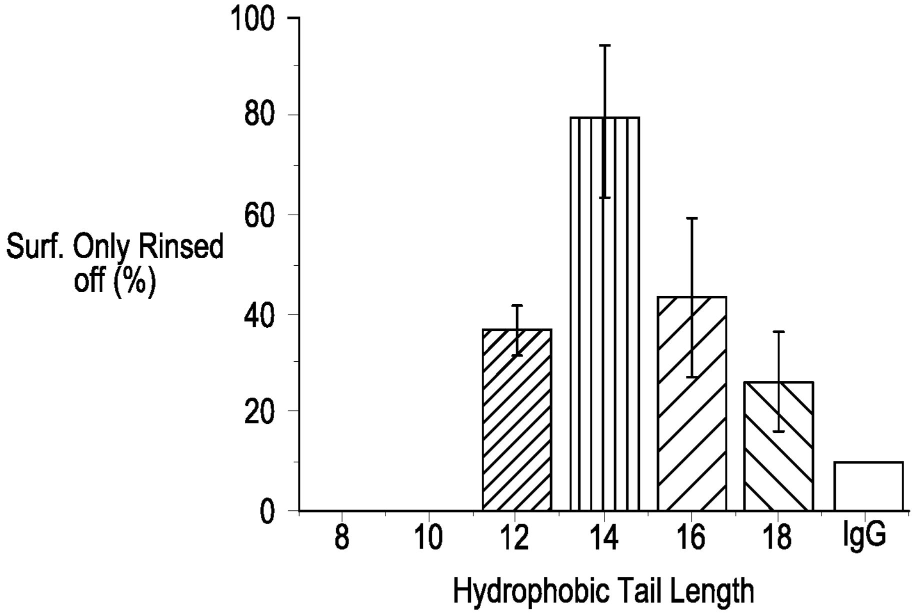
FIG. 4B shows percentage of surfactant alone or IgG alone rinsed off.

Next, a 0.9 wt % saline solution was flowed over the crystal surface to measure how much surfactant can be rinsed off and reversibly desorbed. It was discovered that starting with 14FM1000, the longer the tail, the less surfactant that can be rinsed off (see FIG. 4B). From 8FM1000 to 14FM1000, the longer the tail is, the more percentage of surfactant can be rinsed off (see FIG. 4B). It is believed that surfactant rearrangement on surface for surfactants with shorter and longer tails (comparing with 14FM1000) causes such surfactants to be more irreversibly adsorbed. This is consistent with the DST measurement results. It was also discovered that IgG has minimal reversible adsorption. FIGS. 4A and 4B are QCM-D measurements of surfactant alone samples and IgG alone sample.

Figure 4C:
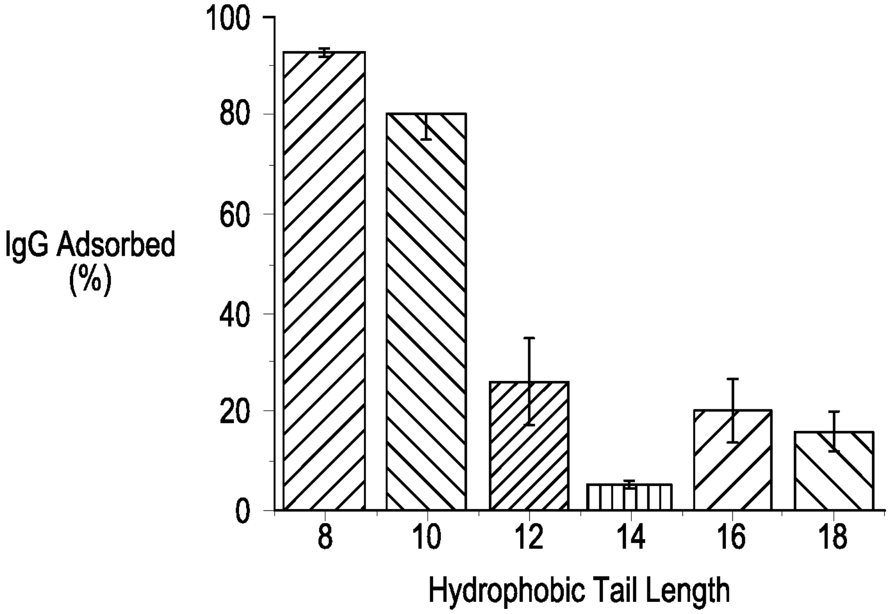
FIG. 4C shows relative amount of IgG adsorbed first calculated by the difference in surfactant with IgG mass adsorbed and surfactant only mass adsorbed, and then normalized to the mass adsorbed for IgG alone sample (100 arbitrary units).
Figure 4D:
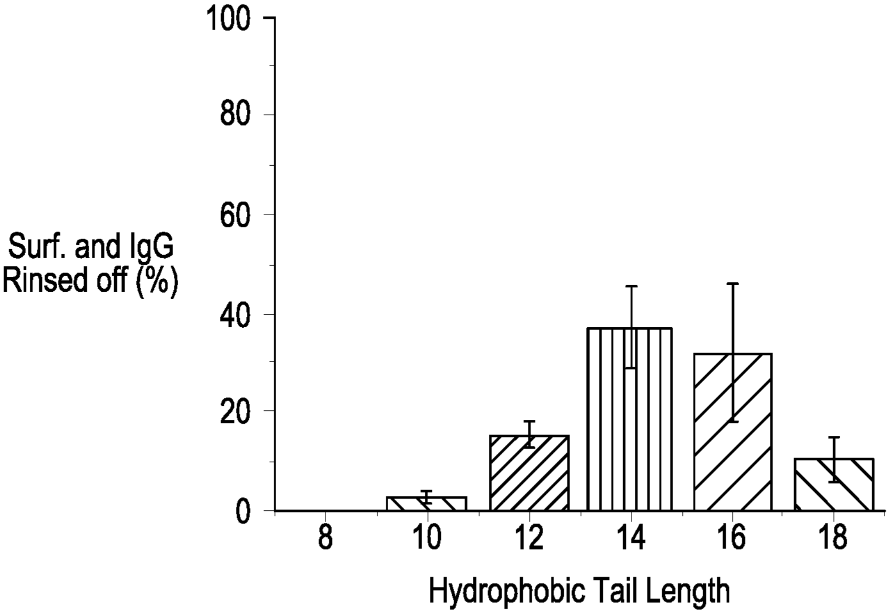
FIG. 4D shows percentage of IgG and surfactant combined mass that can be rinsed off.
Figure 5A:
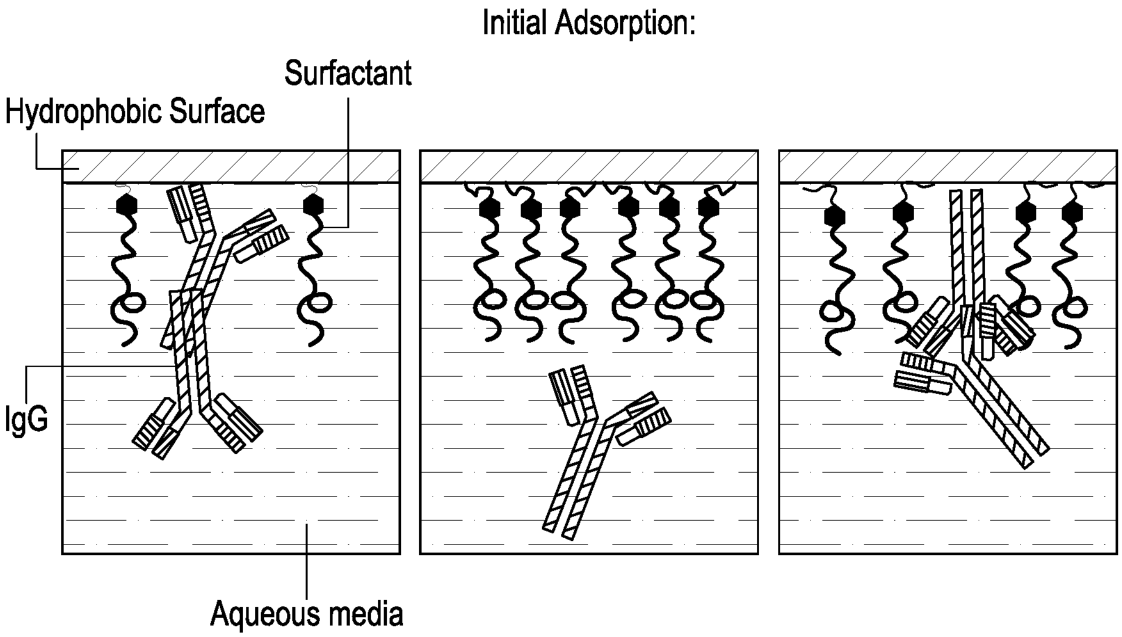
FIG. 5A depicts initial adsorption of surfactants (first decay) elucidated through DST.
Figure 5B:
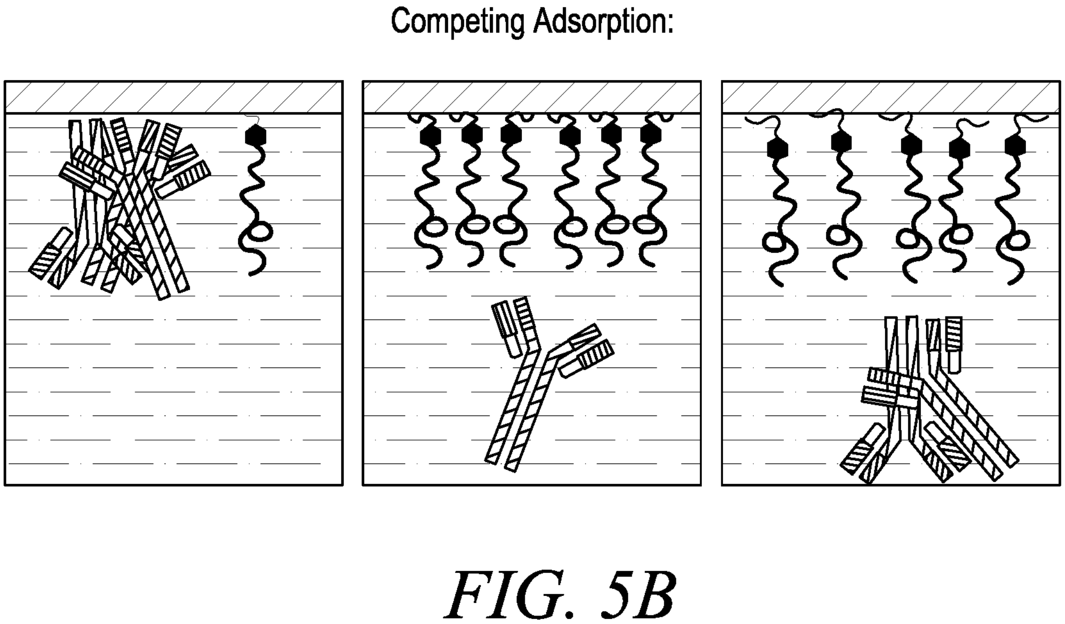
FIG. 5B depicts competing adsorption elucidated through QCM-D.
Figure 5C:
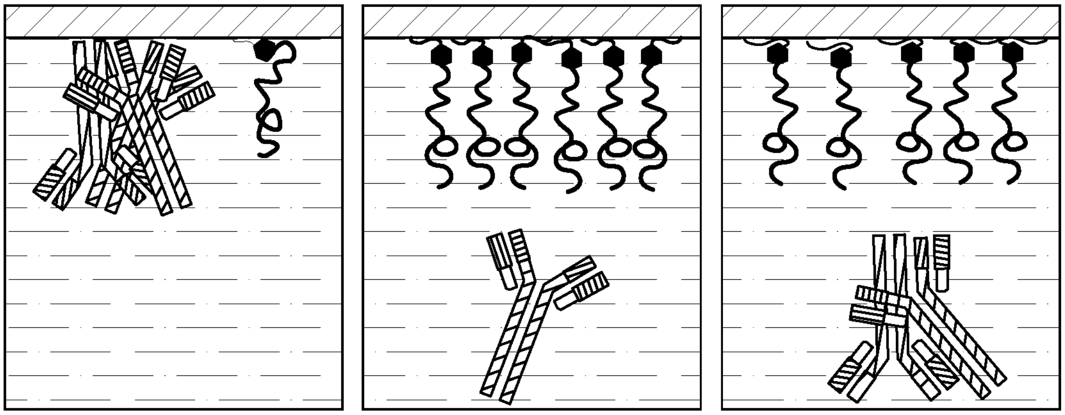
FIG. 5C depicts equilibrium adsorption (second decay) elucidated through the DST.
Figure 5D:
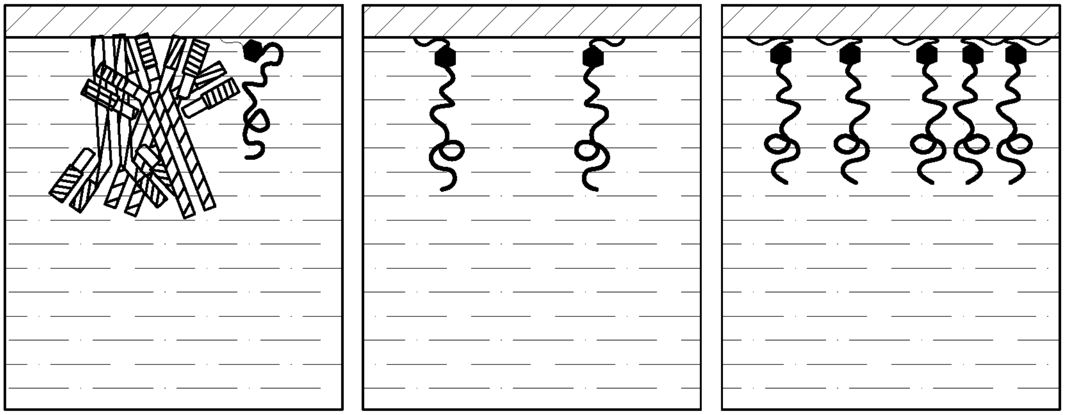
FIG. 5D depicts reversible adsorption elucidated through QCM-D.

Sample solutions containing both IgG and surfactant were flowed over the crystal surface. It is believed that the increase in mass adsorbed relative to when surfactant alone sample is flowed over is due to IgG adsorbed. As shown in FIG. 4C, generally the longer the tail of the surfactant, the less IgG was adsorbed, although for 16FM1000 and 18FM1000, adsorbed IgG was slightly higher, likely due to their slower adsorption kinetics as seen in DST, allowing IgG to outcompete 16FM1000 and 18FM1000 during early times. The relative amount of IgG adsorbed in FIG. 4C was calculated by first subtracting the mass adsorbed for a surfactant alone sample from the mass adsorbed for the corresponding sample containing both surfactant and IgG, and then dividing the subtracted result by the mass adsorbed for IgG alone sample (i.e., the subtracted result was normalized to the mass adsorbed for IgG alone sample (100 arbitrary units)). This data is consistent with the conclusions from DST, that 14FM1000 has an optimal tail length to quickly adsorb and prevent IgG adsorption and/or displace any IgG already adsorbed before it adsorbs irreversibly. Furthermore, when the IgG and surfactant together were rinsed off, we again observed maximum reversible adsorption for the 14FM1000 surfactant compared to the longer and shorter tail lengths due to the irreversible adsorption of surfactant with longer tail lengths or IgG (when surfactant with shorter tail lengths are used) (see FIG. 4D).

The shake study and DST and QCM-D experiments demonstrated that hydrophobic tail length affects surfactant rate, amount, and reversibility of adsorption, which are believed to impact the ability of each surfactant to prevent IgG adsorption and subsequent aggregation (see FIG. 5). For the initial adsorption of surfactants, short tails, such as 8FM1000, have minimum drive to the surface, so few adsorb. Additionally, longer tails such as 18FM1000 are slow to adsorb during the first decay, so IgG adsorbs also. 14FM1000 or other mid-length tails have a fast and strong initial surfactant adsorption (see FIG. 5A). The mid-length tails surfactant 14FM1000 is able to outcompete IgG for adsorption onto the surface due to its ability to quickly adsorb and drop surface tension significantly without rearrangement. Shorter tail surfactants (e.g., 8FM1000) are not adsorbed as strongly likely due to their need to conformationally rearrange to drop surface tension lower. Therefore, IgG is able to outcompete them and begin to aggregate on the surface. Contrastingly, 18FM1000 and other longer tails have a high drive to the surface and can outcompete IgG, but some IgG has already aggregated before sufficient 18FM1000 can arrive (see FIG. 5B). Without wishing to be bound by the theory, it is believed that the hydrophobic tail of 8FM1000 is not sufficiently hydrophobic, so other parts of the surfactant such as the phenylalanine, PPO, or PEO units likely also adsorb. Additionally, the hydrophobic tail of 18FM1000 could change conformations so the long tail will assemble efficiently at the surface. This leads to the equilibrium adsorption that affects surface reversibility (see FIG. 5C). Finally, as shown by a saline rinse in QCM-D, 14FM1000 is more reversibly adsorbed (see FIG. 5D). Without wishing to be bound by the theory, this is believed to be related to the small decrease in surface tension in the second decay, indicating less conformational changes that might make 14FM1000 stick to the surface more. On the other hand, surfactants such as 8FM1000 and 18FM1000 and the IgG try to stabilize and are more irreversibly adsorbed. In addition, the saline rinse simulates the changes in surface area during any movement or shaking such as during transportation, indicating 14FM1000 would be the best at protecting IgG from aggregating on new surfaces that are formed and not getting stuck on otherwise transient surfaces.

It was found that 14FM1000 is able to prevent IgG adsorption, and therefore aggregation, by adsorbing appreciably onto surfaces quickly. 14FM1000 has the fastest rate of initial adsorption compared to the other surfactants studied. Short tail surfactants are slow to and do not adsorb appreciably onto surfaces, allowing IgG adsorption. While long tail surfactants are also slow to adsorb, allowing IgG to adsorb and aggregate, their equilibrium adsorption is strong. Additionally, 14FM1000 is the most reversibly-adsorbed surfactant, likely improving its ability to desorb and adsorb quickly to transient surfaces, therefore protecting the IgG at each new hydrophobic surface and preventing aggregation. Understanding the structure-activity relationship between surfactants and protein stabilization helps to design surfactants with increased stability and utility of protein therapeutics.

Contact Angle Measurements

Contact angle measurements were performed to investigate the protein antifouling activity of 10FM1000, 14FM1000 (FM1000) and 18FM1000 in comparison with polysorbate 80 (PS80) and polysorbate 20 (PS20) on various polymeric surfaces. In bioprocessing, biologics are exposed to multiple polymeric surfaces (tubing, filters, storage containers, etc.) where they can adsorb. This could lead to loss of valuable material, increase in the risk of biologics aggregation, as well as disturbing the structure of therapeutics and perturbance of their function. Surfactants could prevent the fouling of surfaces through fast dynamics at the interfaces. (Wang W. Protein aggregation and its inhibition in biopharmaceutics, Int J Pharm 2005 Jan. 31; 289(1-2): 1-30).

In contact angle measurements, the hydrophilicity of surfaces was assessed by measuring the angle between a water droplet and the surface beneath it. A higher angle indicates a more hydrophobic surface, while a lower one indicates affinity of water to a hydrophilic surface. Different surfaces, which were chosen to represent various bioprocessing materials, were soaked in saline solutions containing Immunoglobulin G (IgG), saline, or a mixture of surfactants with IgG in saline. Saline used here is a 0.9 wt % saline solution (9 g NaCl in 1000 mL MilliQ water). While surfaces tended to have a higher contact angle with the saline control—close to their native behavior—soaking them in IgG alone (in saline) created a hydrophilic coating which decreased the measured contact angle. The contact angle values obtained with saline solutions that contained different concentrations of surfactants (0.001-0.1 mg/mL) fell between those of the saline and IgG controls. Values closer to the saline control indicated the surfactant capacity to prevent protein fouling while those closer to the IgG control showed that protein adsorption on surface was not prevented. Partial protein fouling could be observed at intermediate surfactant concentrations. 14FM1000 activity was compared to derivatives with shorter or longer hydrophobic tails (10FM1000 and 18FM1000) as well as polysorbates.

All surfactant solutions were prepared in saline. Stock solutions of 2 mg/mL were prepared by dissolving 20-40 mg of surfactant in 10-20 mL of saline. They were all stirred at 60° C. until the surfactants were fully dissolved. Solutions were then allowed to return to room temperature before further use. IgG stock solutions were also prepared in saline, usually at 40 mg/mL (6-9 g in 150-225 mL saline), and stirred vigorously to dissolve the protein. All IgG solutions were filtered using a 0.2 μm polyethersulfone filter (PES, ThermoFisher) before dilution in final formulations.

IgG control, saline control, and various saline solutions containing IgG (20 mg/mL) and surfactants (at surfactant concentrations ranging from 0.001 to 0.1 mg/mL), were prepared in vials at a total volume of 15 mL. All final solutions were prepared in saline. Pieces of different surfaces were immersed in the solutions for 24 h at room temperature after which they were dried with nitrogen. Contact angle measurements were performed by dispensing droplets of water on the surfaces (3 μL×4-6 droplets) placed between a camera and a bright background in an Ossila instrument. Images of the sessile drops were captured using an Ossila software (v.1.1.02). The analysis to extract the average contact angle was also performed using an Ossila software (v.3.0.6). For each surface 4 to 6 droplets were averaged using the JMP software (v.15). Results are shown in Tables 1-4.

TABLE 1

Contact Angle Results with Surfactant Concentration of 0.1 mg/mL

| [Surfactant] 0.1 mg/mL | FM1000 | PS80 | PS20 | 18FM1000 | 10FM1000 | Saline control | IgG control |
|---|---|---|---|---|---|---|---|
| PES | 68.9 | 70.8 | 67.3 | 71.0 | 13.0 | 58.5 | 13.9 |
| PE | 64.7 | 36.9 | 59.7 | 63.7 | 19.0 | 71.3 | 18.5 |
| PVDF | 75.2 | 77.3 | 78.6 | 12.5 | 12.9 | 73.3 | 14.3 |
| IV Bag (PVC) | 92.1 | 95.0 | 90.9 | 92.7 | 52.5 | 96.5 | 15.6 |
| Silicone | 115.5 | 111.6 | 109.5 | 108.3 | 94.9 | 108.7 | 23.5 |
| PTFE | 97.0 | 101.1 | 105.4 | 100.6 | 82.6 | 92.2 | 20.3 |

TABLE 2

Contact Angle Results with Surfactant Concentration of 0.05 mg/mL

| [Surfactant] 0.05 mg/mL | FM1000 | PS80 | PS20 | 18FM1000 | 10FM1000 | Saline control | IgG control |
|---|---|---|---|---|---|---|---|
| PES | 66.4 | 65.3 | 69.5 | 66.2 | 15.2 | 58.5 | 13.9 |
| PE | 47.4 | 20.2 | 37.5 | 60.5 | 18.5 | 71.3 | 18.5 |
| PVDF | 69.9 | 36.2 | 70.9 | 22.4 | 12.6 | 73.3 | 14.3 |
| IV Bag (PVC) | 87.8 | 86.5 | 91.7 | 82.7 | 21.1 | 96.5 | 15.6 |
| Silicone | 115 | 112.5 | 105.1 | 105.2 | 33.7 | 108.7 | 23.5 |
| PTFE | 99.6 | 90.3 | 100.8 | 98.4 | 28.1 | 92.2 | 20.3 |

TABLE 3

Contact Angle Results with Surfactant Concentration of 0.02 mg/mL

| [Surfactant] 0.02 mg/mL | FM1000 | PS80 | PS20 | 18FM1000 | 10FM1000 | Saline control | IgG control |
|---|---|---|---|---|---|---|---|
| PES | 49.0 | 24.0 | 54.5 | 67.7 | 15.5 | 58.5 | 13.9 |
| PE | 27.3 | 19.2 | 20.7 | 53.1 | 20.2 | 71.3 | 18.5 |
| PVDF | 35.5 | 17.5 | 18.7 | 42.3 | 12.7 | 73.3 | 14.3 |
| IV Bag (PVC) | 91.0 | 55.7 | 64.8 | 82.4 | 21.2 | 96.5 | 15.6 |
| Silicone | 107.9 | 72.3 | 96.9 | 58.7 | 21.7 | 108.7 | 23.5 |
| PTFE | 97.5 | 66.1 | 90.2 | 90.0 | 18.3 | 92.2 | 20.3 |

TABLE 4

Contact Angle Results with Surfactant Concentration of 0.001 mg/mL

| [Surfactant] 0.001 mg/mL | FM1000 | PS80 | PS20 | 18FM1000 | 10FM1000 | Saline control | IgG control |
|---|---|---|---|---|---|---|---|
| PES | 13.9 | 10.0 | 14.6 | 14.7 | 17.5 | 58.5 | 13.9 |
| PE | 15.7 | 17.4 | 25.2 | 18.0 | 21.2 | 71.3 | 18.5 |
| PVDF | 14.9 | 12.5 | 14.0 | 15.9 | 13.6 | 73.3 | 14.3 |
| IV Bag (PVC) | 18.7 | 17.6 | 19.1 | 22.3 | 19.8 | 96.5 | 15.6 |
| Silicone | 33.1 | 34.8 | 28.9 | 25.9 | 24.5 | 108.7 | 23.5 |
| PTFE | 17.0 | 24.9 | 18.9 | 19.1 | 22.1 | 92.2 | 20.3 |

Notes to Tables 1-4: (1) All solutions, besides the saline control, contained 20 mg/mL IgG. (2) The saline control was 0.9% saline without IgG and surfactant. (3) The IgG control was 20 mg/mL IgG in 0.9% saline without surfactant. (4) PVC is polyvinyl chloride. (5) PES, PE, PVDF, PVC, Silicone and PTFE denote the polymeric materials of the surfaces.

Surface Loss Measurements on Filters and Chromatography Columns

In downstream processing, biologic therapeutics are subjected to multiple purification steps. These consist of a number of chromatography columns and filters where increased interactions could lead to protein adsorption or aggregation (Li et al., Protein Instability at Interfaces During Drug Product Development—Fundamental Understanding, Evaluation, and Mitigation. AAPS series, Springer 2021. ISSN 2210-7371). Surfactants, such as polysorbates, could help in stabilizing these proteins but are usually added in formulation post-processing since they can adsorb to surfaces (Zhou et al., Non-specific binding and saturation of Polysorbate-20 with aseptic filter membranes for drug substance and drug product during mAb production. Journal of Membrane Science 2008, 325 (2), 735-741; Mahler et al., Adsorption Behavior of a Surfactant and a Monoclonal Antibody to Sterilizing-Grade Filters. Journal of Pharmaceutical Sciences 2010, 99 (6), 2620-2627). A suggested solution for this problem consists of pre-saturating filter membranes with the surfactant. However, this is not always feasible as a retained volume of buffer within the filter could lead to diluting the protein product. This preventative measure could thus require flushing with a solution that contains both the surfactant and the product, as to not dilute the latter (Mahler et al., Adsorption Behavior of a Surfactant and a Monoclonal Antibody to Sterilizing-Grade Filters. Journal of Pharmaceutical Sciences 2010, 99 (6), 2620-2627) leading to loss of valuable product and lower yield.

For successful implementation of surfactants in bioprocessing, it is thus desirable to search for molecules that adhere less to filter and column materials. Another important factor is to examine the integrity of the surfactant after it encounters the purification surface to ensure that its activity is preserved. Here, surfactant solutions were flushed through widely used filters (PVDF, PES) and columns (sulfopropyl-functionalized cross-linked agarose, Protein A and quaternary ammonium-functionalized cross-linked agarose) and the filtrate and eluate were examined using liquid chromatography. The elution of 14FM1000 and its derivatives with shorter and longer tails was compared to that of polysorbate 80 (PS80). Examining the chromatograms of polysorbate 80 revealed partial recovery at first followed by an inconsistent full recovery.

In surface loss studies, surfactant solutions were prepared at 0.03 mg/mL (30 ppm) in milliQ water by diluting stock solutions prepared at 1 mg/mL in water. Syringes (Becton Dickinson, BD Luer-Lok™ 3 mL or 10 mL) were used to flow the solutions through the filters or chromatography columns. As it was observed that syringe surfaces could retain surfactants, they were all pre-washed with 3× syringe volume using the 0.03 mg/mL surfactant solution. Once the syringe was washed and filled with fresh surfactant solution, around 100-200 mg of the solution was delivered to vials (12×32 mm, Thermo Scientific) containing low-volume inserts (Thermo Scientific). The first sample was always collected directly from the syringe without passing through any filter or column as it provided a control to which the subsequent filtrates were compared. In filter studies, the syringe was attached to a needle (BD 21 G, 0.8 mm×50 mm) which facilitated the delivery of the solutions to the bottom of the inserts. The needle was purged with air after collecting the control to empty it from any remaining solution, and attached to the filter exit. Filtrates were also collected at intervals of around 100-200 mg in pre- and post-weighed vials for accurate determination of solution weights. In column experiments, the columns were pre-washed with around 15-column volumes of water to remove the storage solution and condition them. They were then attached to pre-washed syringes (rinsed with surfactant solutions, like with the filters) containing 0.03 mg/mL solutions of surfactants and elution was performed using a vertically positioned syringe pump (Kd Scientific) which was set to deliver solutions at a recommended rate of 1 mL/min. Sample collection was performed at intervals similar to the filter studies, and the solution weights were accurately determined.

Surfactant quantification was performed on a high-performance liquid chromatography (HPLC) system (Vanquish, Thermo Scientific) equipped with a charged aerosol detector (CAD) controlled by a Chromeleon software (v 7.3, Thermo Scientific). All samples were loaded in the autosampler chamber which was set at 20° C. An Acclaim™ Surfactant Column (Thermo Scientific, 3×150 mm, particle size 3 μm) was used for separation with a mobile phase that contained 10 mM ammonium acetate (LC-MS grade, Sigma Aldrich) in water fixed at pH 5 and acetonitrile (J. T. Baker). Elution was set to 0.6 mL/min starting with 90% of the aqueous mobile phase followed by ramping up to 95% acetonitrile with the transition between the two solutions taking place over 2 min. Surfactants elution occurred in the presence of the highly organic mobile phase. Surfactant calibration curves prepared from the stock solutions in concentrations ranging from 0.06 mg/mL to 0.0005 mg/mL were also measured with the same method and used to quantify surfactants in the filtrate aliquots. MilliQ water signal was subtracted from all sample chromatograms. All analyses were performed on the Chromeleon software, followed by calculations on Excel and JMP v.15. Results are shown in FIGS. 6-9.

Figure 6B:
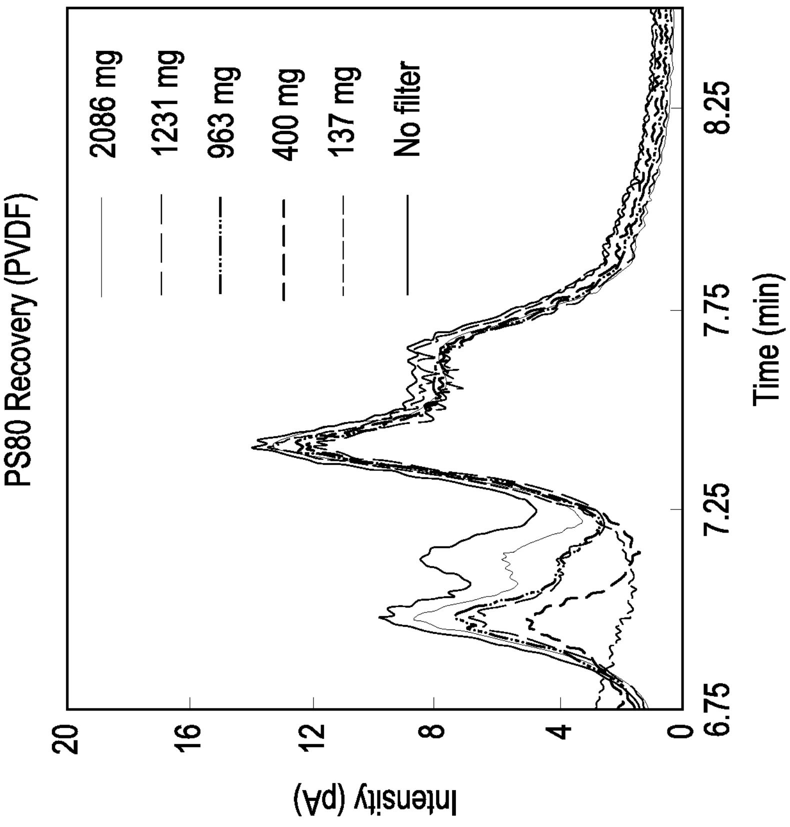
FIGS. 6A and 6B show examples of FM1000 and PS80 chromatograms sampled at different points during filtration. Weights in mg at the right side of the graphs represent cumulative weights of the filtrate, and chromatograms represent filtrate aliquots with cumulative weights up to about 2000 mg.
Figure 6A:
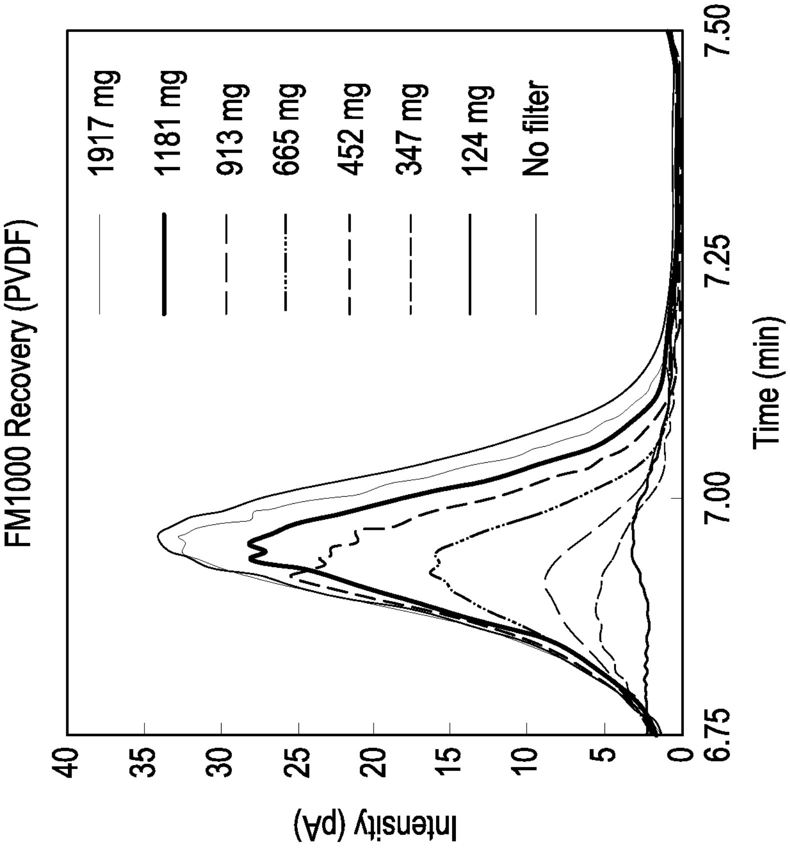

FIG. 6 shows the surfactant loss when passing through the PVDF filter. While FM1000 peak was largely unchanged, PS80 came out in 4 peaks, of which the two rightmost were present immediately after passing through the filter while the two on the left varied through the filtration (see FIG. 6B). This demonstrated that some components (represented by the two rightmost peaks) in the PS80 composition are not adsorbed on the PVDF filter while the other components (represented by the two leftmost peaks) in the PS80 composition are adsorbed and lost on the PVDF filter. Therefore, the PS80 composition and property are changed during the filtration. In comparison, FM1000 passed through the PVDF filter as a uniform peak (see FIG. 6A). This demonstrated that the FM1000 composition and property are not changed during the filtration.

Figure 7B:
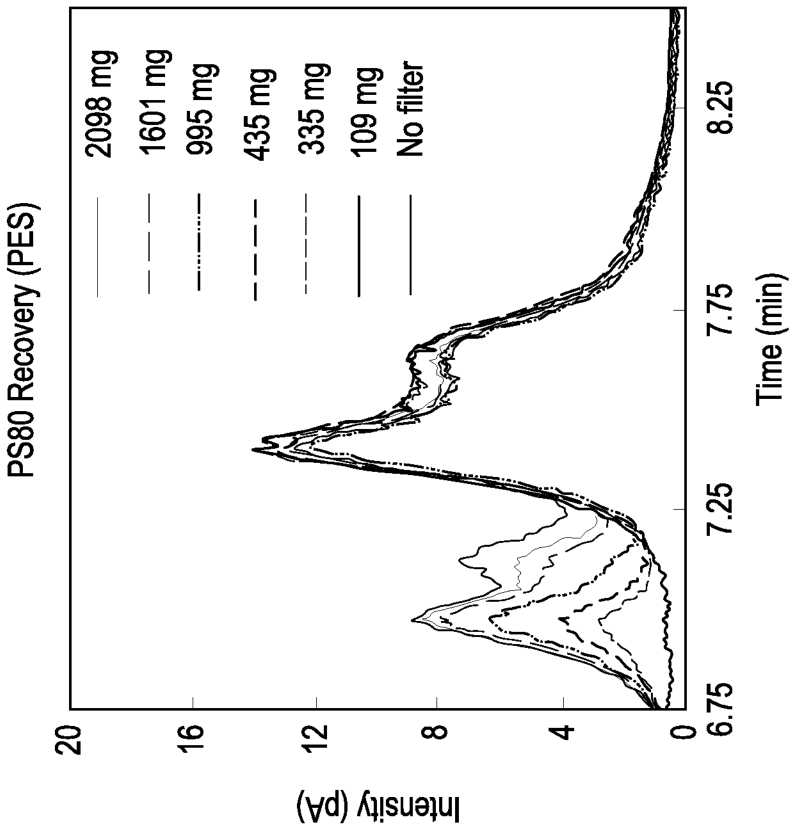
FIGS. 7A and 7B show examples of FM1000 and PS80 chromatograms sampled at different points during filtration. Weights in mg at the right side of the graphs represent cumulative weights of the filtrate, and chromatograms represent filtrate aliquots with cumulative weights up to about 2000 mg.
Figure 7A:
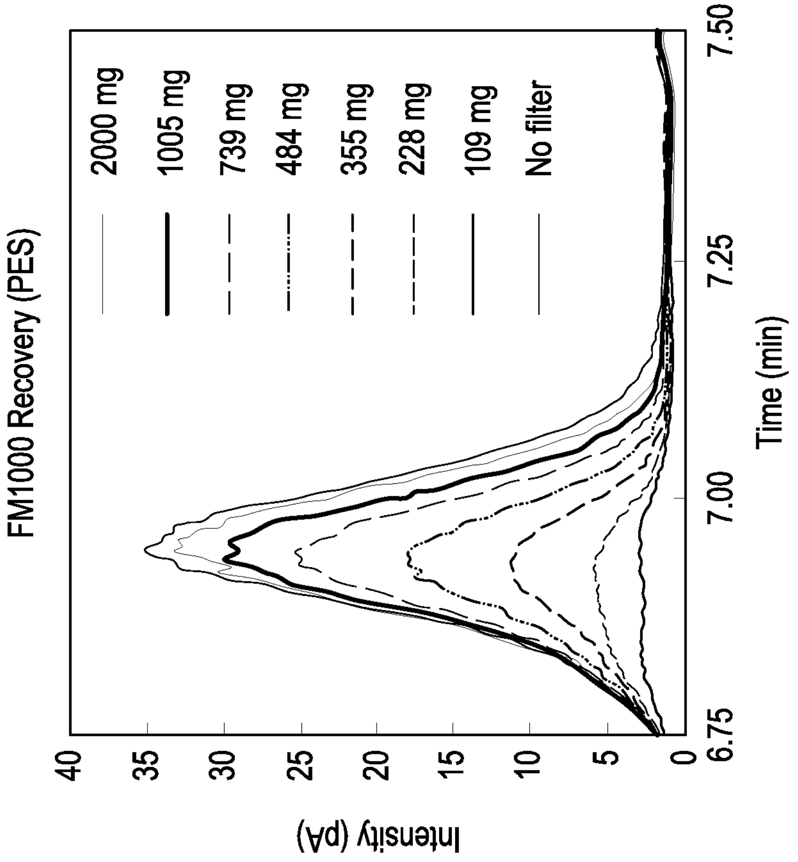

FIG. 7 shows the surfactant loss when passing through the PES filter. While FM1000 peak was largely unchanged, PS80 came out in 4 peaks, of which the two rightmost were present immediately after passing through the filter while the two on the left varied through the filtration (see FIG. 7B). This demonstrated that some components (represented by the two rightmost peaks) in the PS80 composition are not adsorbed on the PES filter while the other components (represented by the two leftmost peaks) in the PS80 composition are adsorbed and lost on the PES filter. Therefore, the PS80 composition and property are changed during the filtration. In comparison, FM1000 passed through the PES filter as a uniform peak (see FIG. 7A). This demonstrated that the FM1000 composition and property are not changed during the filtration.

Figure 8A:
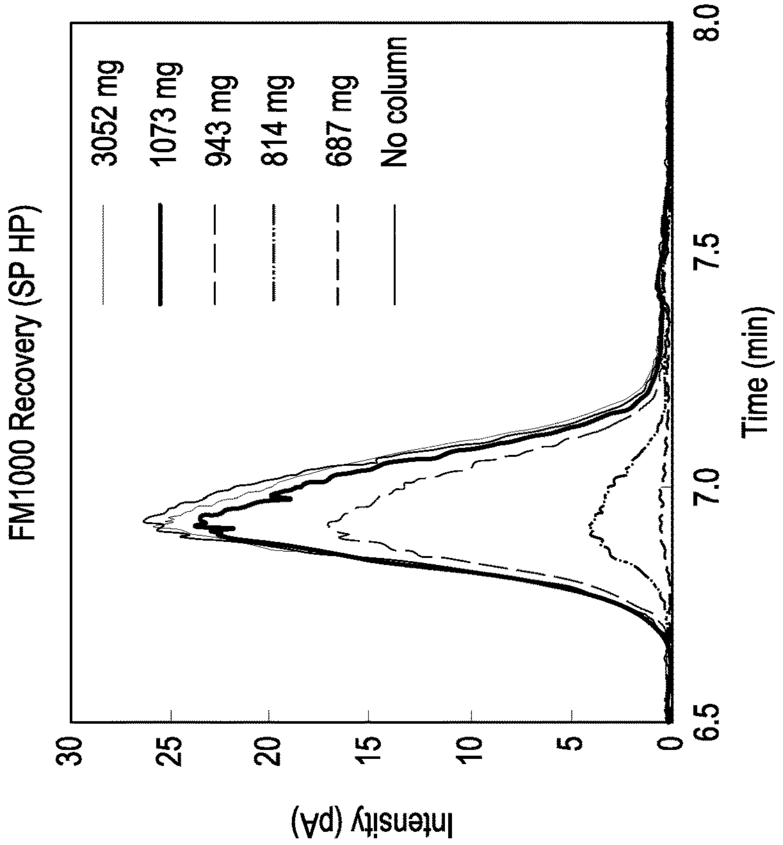
FIGS. 8A and 8B show examples of FM1000 and PS80 chromatograms sampled at different points during the elution. Weights in mg at the right side of the graphs represent cumulative weights of the eluate, and chromatograms represent eluate aliquots with cumulative weights up to about 3000 mg.
Figure 8B:
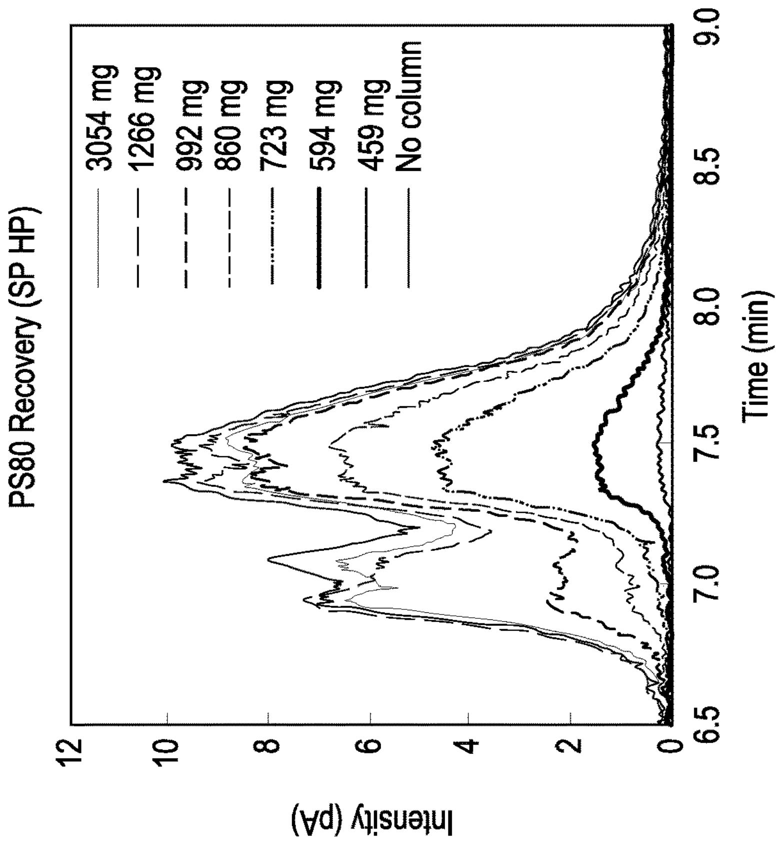

FIG. 8 shows the surfactant loss when passing through the sulfopropyl-functionalized cross-linked agarose (SP HP) chromatography column. While FM1000 peak was largely unchanged, PS80 came out in 4 peaks, of which the two rightmost were present much sooner after passing through the column than the two on the left (see FIG. 8B). This demonstrated that some components (represented by the two rightmost peaks) in the PS80 composition are not adsorbed on the sulfopropyl-functionalized cross-linked agarose column while the other components (represented by the two leftmost peaks) in the PS80 composition are adsorbed and lost on the sulfopropyl-functionalized cross-linked agarose column. Therefore, the PS80 composition and property are changed during the chromatography. In comparison, FM1000 passed through the sulfopropyl-functionalized cross-linked agarose column as a uniform peak (see FIG. 8A). This demonstrated that the FM1000 composition and property are not changed during the chromatography.

Figure 9A:
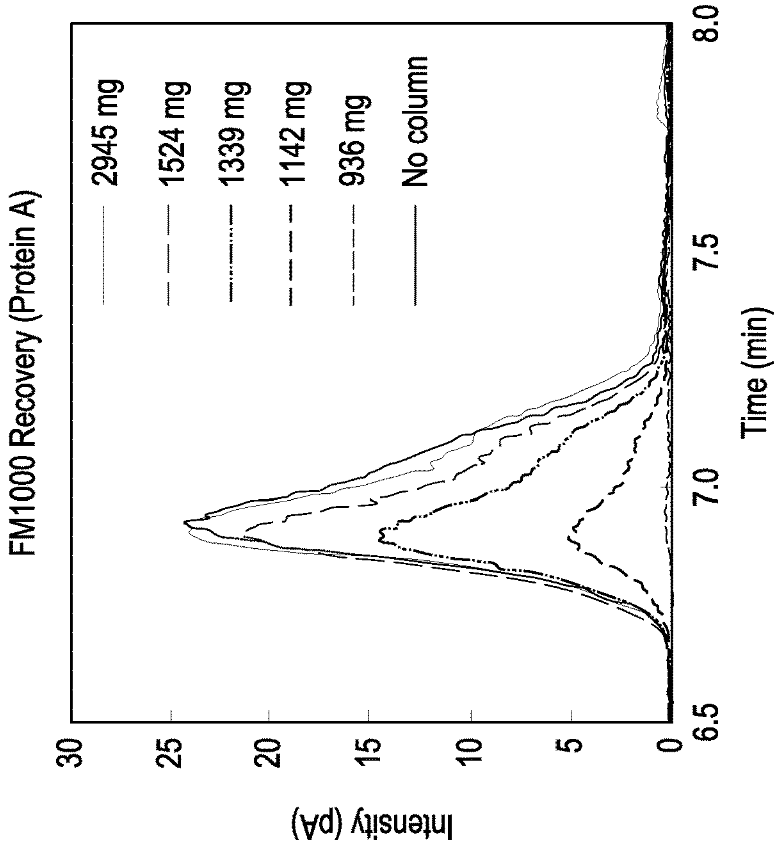
FIGS. 9A and 9B show examples of FM1000 and PS80 chromatograms sampled at different points during the elution. Weights in mg at the right side of the graphs represent cumulative weights of the eluate, and chromatograms represent eluate aliquots with cumulative weights up to about 3000 mg.
Figure 9B:
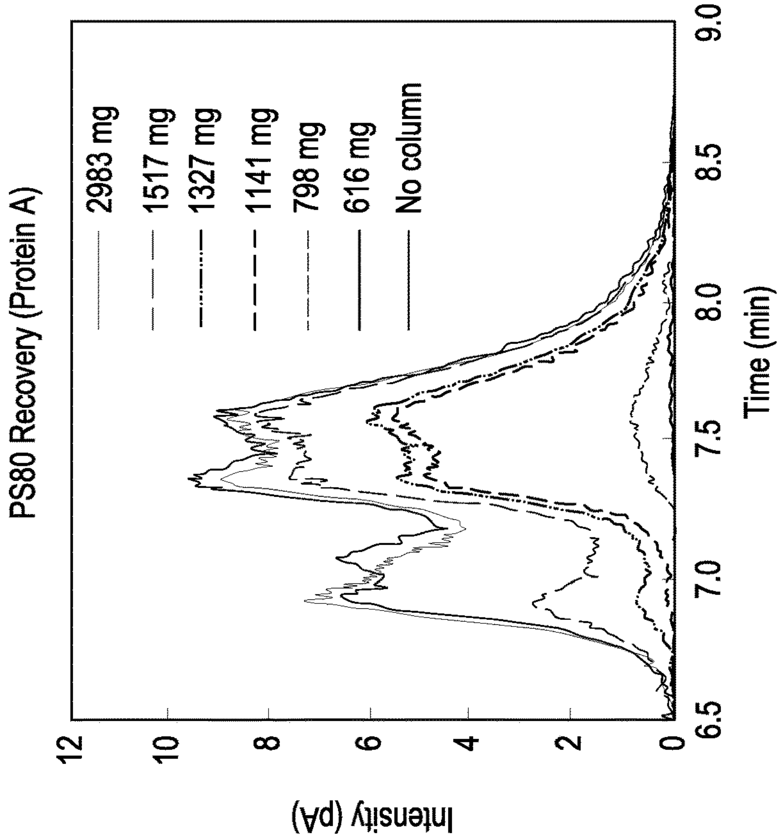

FIG. 9 shows the surfactant loss when passing through the Protein A chromatography column. While FM1000 peak was largely unchanged, PS80 came out in 4 peaks, of which the two rightmost were present much sooner after passing through the column than the two on the left (see FIG. 9B). This demonstrated that some components (represented by the two rightmost peaks) in the PS80 composition are not adsorbed on the Protein A column while the other components (represented by the two leftmost peaks) in the PS80 composition are adsorbed and lost on the Protein A column. Therefore, the PS80 composition and property are changed during the chromatography. In comparison, FM1000 passed through the Protein A column as a uniform peak (see FIG. 9A). This demonstrated that the FM1000 composition and property are not changed during the chromatography.

Figure 10A:
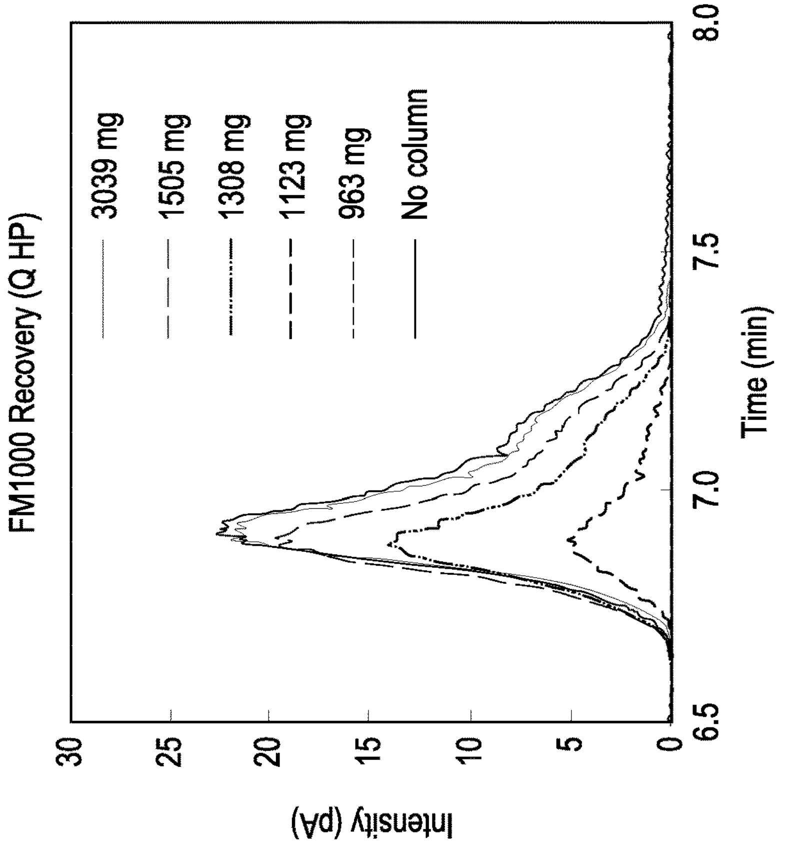
FIGS. 10A and 10B show examples of FM1000 and PS80 chromatograms sampled at different points during the elution. Weights in mg at the right side of the graphs represent cumulative weights of the eluate, and chromatograms represent eluate aliquots with cumulative weights up to about 3000 mg.
Figure 10B:
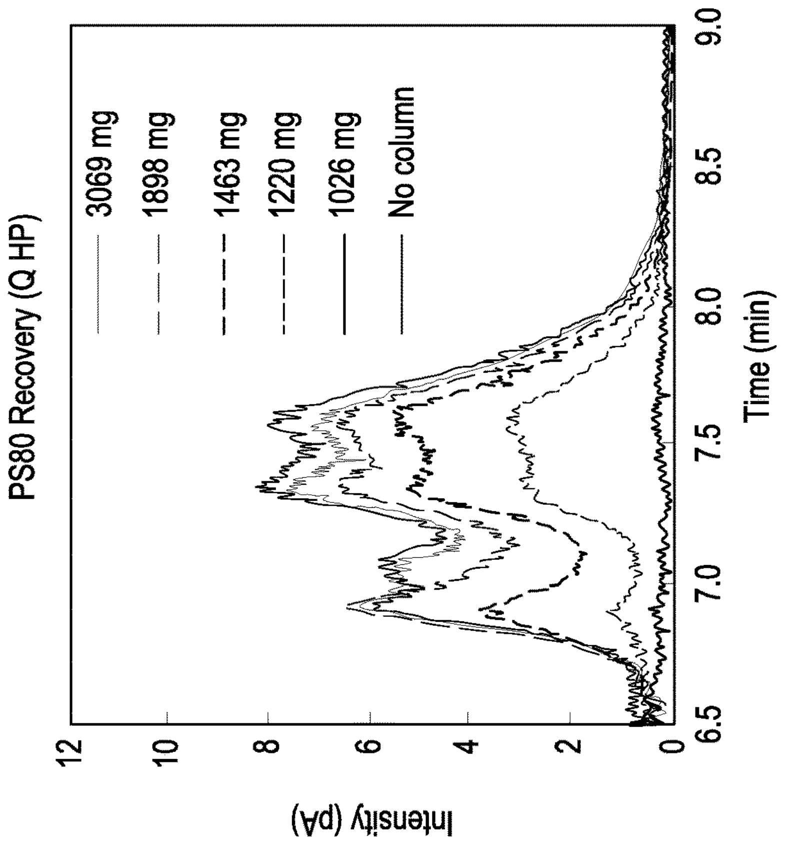

FIG. 10 shows the surfactant loss when passing through the quaternary ammonium-functionalized cross-linked agarose (Q HP) chromatography column. While FM1000 peak was largely unchanged, PS80 came out in 4 peaks, of which the two rightmost were present much sooner after passing through the column than the two on the left (see FIG. 10B). This demonstrated that some components (represented by the two rightmost peaks) in the PS80 composition are not adsorbed on the quaternary ammonium-functionalized cross-linked agarose column while the other components (represented by the two leftmost peaks) in the PS80 composition are adsorbed and lost on the quaternary ammonium-functionalized cross-linked agarose column. Therefore, the PS80 composition and property are changed during the chromatography. In comparison, FM1000 passed through the quaternary ammonium-functionalized cross-linked agarose column as a uniform peak (see FIG. 10A). This demonstrated that the FM1000 composition and property are not changed during the chromatography.

Analysis were conducted to find out how much volume of the surfactant solutions were required to reach 90 wt % of the surfactant quantity. In other words, the cumulative amount of surfactant contained in the filtrate/eluate were analyzed and calculated to find out at which point (filtrate/eluate volume) the cumulative amount of surfactant (contained in the filtrate/eluate) reaches 90 wt % of the total amount of surfactant (contained in the surfactant solution) fed to the filter/column. The results are summarized in Table 5.

In Table 5, the top row indicates the kind of surfactant and the left column indicates the kind of filter or chromatography column. The quantities in the table indicate the volume (in mL) of filtrate/eluate required to reach 90±1 wt % of surfactant recovery in the filtrate/eluate. The higher the volume, the longer it takes for the surfactant to recover in the filtrate/eluate. In Table 5, volume values were obtained by integrating the HPLC-CAD peaks of each component in filtrate/eluate aliquots and then dividing them by their quantity in samples that were not filtered or passed through a column, taken as 100%. Volume values were noted for the first aliquot that reached the 90 wt % threshold in each run.

TABLE 5

| | FM1000 | PS80 | 10FM1000 | 18FM1000 |
|---|---|---|---|---|
| PVDF filter | 1.68 | 2.16 | 0.14 | 1.66 |
| PES filter | 1.51 | 1.35 | 0.24 | 1.09 |
| SP HP column | 1.07 | 1.27 | 1.22 | 1.61 |
| Q HP column | 1.50 | 2.34 | 1.36 | 1.82 |
| Protein A column | 1.73 | 2.05 | 1.64 | 1.93 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A process comprising:

(a) providing an aqueous solution comprising a protein and a polyalkoxy fatty acyl surfactant of formula I (I)

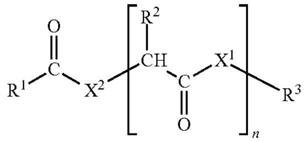

wherein $R^1$—C(═O) is a fatty acyl group, $R^2$ is H or a substituted or unsubstituted hydrocarbyl group, $X^1$ is O or NH, $X^2$ is O or NH, n is 0, 1, 2, 3, 4, or 5, $R^3$ is a polymeric group comprising polymerized units of formula II and III (II)

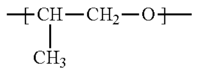

(III)

$$-\!\!\left[CH_2-CH_2-O\right]\!\!-$$

(b) subjecting the aqueous solution to a bioprocess comprising:

filtering the aqueous solution with a filter selected from the group consisting of a polyvinylidene fluoride (PVDF) filter, a polyethersulfone (PES) filter, a polypropylene filter, a cellulose filter, a nylon filter, and any combination thereof to produce a first filtrate, and subjecting the first filtrate to a chromatography column comprising a chromatography resin selected from the group consisting of sulfopropyl-functionalized cross-linked agarose, Protein A, quaternary ammonium-functionalized cross-linked agarose, a hydrophobic interaction chromatography resin, and any combinations thereof to produce a second filtrate, wherein the filter exhibits reduced fouling by the protein as compared to a filter subjected to the bioprocess with the aqueous solution having polysorbate 80 in place of the polyalkoxy fatty acyl surfactant.

2. The process of claim 1 wherein the polyalkoxy fatty acyl surfactant of formula I is selected from the group consisting of 12FM1000, FM1000, 16FM1000, 18FM1000, and mixtures thereof.

3. The process of claim 1 wherein the polyalkoxy fatty acyl surfactant of formula I is FM1000.

4. The process of claim 1 wherein the polyalkoxy fatty acyl surfactant of formula I is selected from the group consisting of FM1000, 16FM1000, 18FM1000, and mixtures thereof.

5. The process of claim 1 wherein the filter is a PVDF filter or a PES filter.

6. The process of claim 1 wherein the polyalkoxy fatty acyl surfactant of formula I in the first filtrate produces a single-peak chromatogram following the filtering as measured by a high-performance liquid chromatography system equipped with a charged aerosol detector and a mobile phase comprising 10 mM ammonium acetate in water at pH 5 and acetonitrile.

7. The process of claim 1 wherein the chromatography resin is selected from the group consisting of sulfopropyl-functionalized cross-linked agarose, Protein A, and quaternary ammonium-functionalized cross-linked agarose.

8. The process of claim 1 wherein step (b) further comprises transporting the aqueous solution.

9. The process of claim 8 wherein the polyalkoxy fatty acyl surfactant of formula I is selected from the group consisting of 12FM1000, FM1000, and mixtures thereof.

10. The process of claim 9 wherein the polyalkoxy fatty acyl surfactant of formula I is FM1000.

11. The process of claim 1, wherein the polyalkoxy fatty acyl surfactant is present in the aqueous solution at a concentration from 0.01 mg/mL to 0.05 mg/mL based on the total volume of the aqueous solution.

12. The process of claim 1, wherein the polyalkoxy fatty acyl surfactant is present in the aqueous solution at a concentration of no more than 0.1 mg/mL based on the total volume of the aqueous solution.

13. The process of claim 1, wherein $X^1$ is NH and wherein $X^2$ is NH.

14. The process of claim 1, wherein the protein comprises IgG.

15. The process of claim 1, wherein the polyalkoxy fatty acyl surfactant of formula I is FM1000, and wherein the concentration of the FM1000 is from 0.03 mg/mL to 0.05 mg/mL based on the total volume of the aqueous solution.

* * * * *